(12) United States Patent
Pan et al.

(10) Patent No.: US 9,469,667 B2
(45) Date of Patent: Oct. 18, 2016

(54) METAL COMPLEXES

(75) Inventors: Junyou Pan, Frankfurt am Main (DE); Amir Hossain Parham, Frankfurt am Main (DE)

(73) Assignee: Merck Patent GmbH (DE)

( * ) Notice: Subject to any disclaimer, the term of this patent is extended or adjusted under 35 U.S.C. 154(b) by 27 days.

(21) Appl. No.: 14/009,445

(22) PCT Filed: Mar. 7, 2012

(86) PCT No.: PCT/EP2012/001017
§ 371 (c)(1),
(2), (4) Date: Oct. 2, 2013

(87) PCT Pub. No.: WO2012/136296
PCT Pub. Date: Oct. 11, 2012

(65) Prior Publication Data
US 2014/0045810 A1    Feb. 13, 2014

(30) Foreign Application Priority Data
Apr. 4, 2011 (EP) .................................... 11002802

(51) Int. Cl.
| C07F 15/00 | (2006.01) |
| H01L 51/00 | (2006.01) |
| C09K 11/06 | (2006.01) |
| H05B 33/14 | (2006.01) |
| H01L 51/50 | (2006.01) |

(52) U.S. Cl.
CPC ....... *C07F 15/0086* (2013.01); *C07F 15/0033* (2013.01); *C09K 11/06* (2013.01); *H01L 51/0085* (2013.01); *H01L 51/0087* (2013.01); *H05B 33/145* (2013.01); *C09K 2211/1007* (2013.01); *C09K 2211/1029* (2013.01); *C09K 2211/1044* (2013.01); *C09K 2211/1059* (2013.01); *C09K 2211/1088* (2013.01); *C09K 2211/185* (2013.01); *H01L 51/0058* (2013.01); *H01L 51/0059* (2013.01); *H01L 51/0067* (2013.01); *H01L 51/0077* (2013.01); *H01L 51/0094* (2013.01); *H01L 51/5016* (2013.01); *Y02E 10/549* (2013.01)

(58) Field of Classification Search
CPC .......... C07F 15/0033; C07F 15/0086; H01L 51/0087; H01L 51/0085; H05B 33/145; C09K 11/06
USPC ................... 544/64, 225; 546/2; 252/301.16
See application file for complete search history.

(56) References Cited

U.S. PATENT DOCUMENTS

| 8,674,343 B2 | 3/2014 | Lecloux et al. |
| 8,945,725 B2 | 2/2015 | Takizawa et al. |
| 8,960,979 B2 | 2/2015 | Sanchez et al. |
| 9,169,282 B2 | 10/2015 | Stoessel et al. |
| 2013/0051011 A1 | 2/2013 | Janssen et al. |

FOREIGN PATENT DOCUMENTS

| JP | 2009-102533 A | 5/2009 |
| JP | 2011-052087 A | 3/2011 |
| JP | 2011-054695 A | 3/2011 |
| JP | 2013-509715 A | 3/2013 |
| JP | 2013-519971 A | 5/2013 |
| JP | 2013-519972 A | 5/2013 |
| WO | WO-00/70655 A2 | 11/2000 |
| WO | 2009/047993 A1 | 4/2009 |
| WO | 2010/032663 A1 | 3/2010 |
| WO | 2010/086089 A1 | 8/2010 |
| WO | WO-2011024968 A1 | 3/2011 |
| WO | WO-2011025068 A1 | 3/2011 |

OTHER PUBLICATIONS

International Search Report for PCT/EP2012/001017 mailed May 25, 2012.
English Translation of Japanese Office Action for Application No. 2014-503008 dated Sep. 8, 2015.
European Office Action for Application No. 12707709.7 dated Jan. 22, 2016.

*Primary Examiner* — Porfirio Nazario Gonzalez
(74) *Attorney, Agent, or Firm* — Drinker Biddle & Reath LLP

(57) ABSTRACT

The present invention relates to metal complexes and to electronic devices, in particular organic electroluminescent devices, comprising these metal complexes.

16 Claims, 3 Drawing Sheets

METAL COMPLEXES

CROSS-REFERENCE TO RELATED APPLICATIONS

This application is a national stage application (under 35 U.S.C. §371) of PCT/EP2012/001017, filed Mar. 7, 2012, which claims benefit of European application 11 002 802.4, filed Apr. 4, 2011.

The present invention relates to metal complexes which are suitable for use as emitters in organic electroluminescent devices.

The structure of organic electroluminescent devices (OLEDs) in which organic semiconductors are employed as functional materials is described, for example, in U.S. Pat. No. 4,539,507, U.S. Pat. No. 5,151,629, EP 0676461 and WO 98/27136. The emitting materials employed here are increasingly organometallic complexes which exhibit phosphorescence instead of fluorescence (M. A. Baldo et al., *Appl. Phys. Lett.* 1999, 75, 4-6). For quantum-mechanical reasons, an up to four-fold energy and power efficiency is possible using organometallic compounds as phosphorescence emitters. In general, there is still a need for improvement in the case of OLEDs which exhibit triplet emission, in particular with respect to efficiency, operating voltage and lifetime. This applies, in particular, to OLEDs which emit in the relatively short-wave region, i.e. green and in particular blue.

The triplet emitters employed in accordance with the prior art in phosphorescent OLEDs are, in particular, iridium complexes. For example, iridium complexes are known which contain imidazophenanthridine derivatives or diimidazoquinazoline derivatives as ligands (WO 2007/095118). These complexes can result in blue phosphorescence on use in organic electroluminescent devices, depending on the precise structure of the ligand. Here too, further improvements with respect to efficiency, operating voltage and lifetime are still desirable. Furthermore, there is also still a need for improvement here with respect to the colour coordinates in order to be able to achieve deep-blue emission.

The object of the present invention is therefore the provision of novel metal complexes which are suitable as emitters for use in OLEDs. In particular, the object is to provide emitters which are also suitable for blue-phosphorescent OLEDs, and emitters which exhibit improved properties with respect to efficiency, operating voltage, lifetime and/or colour coordinates.

Surprisingly, it has been found that the metal chelate complexes described in greater detail below, which contain a bridged ligand which contains a nitrogen atom in the para-position to the carbon atom bonded to the metal, achieve this object and result in improvements in the organic electroluminescent device. The present invention therefore relates to these metal complexes and to organic electroluminescent devices which comprise these complexes.

The invention thus relates to a compound of the formula (1),

where the compound of the general formula (1) contains a moiety $M(L)_n$ of the formula (2):

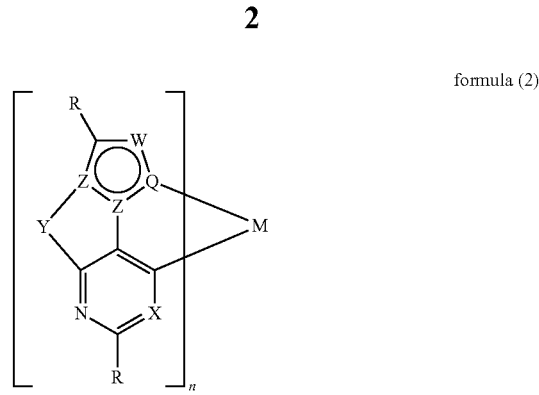

formula (2)

where the following applies to the symbols and indices used:

M is a transition metal;
Q is on each occurrence, identically or differently, N or C;
X is on each occurrence, identically or differently, CR or N;
Y is on each occurrence, identically or differently, a substituted or unsubstituted diatomic bridge containing, as bridge atoms, two atoms selected, identically or differently on each occurrence, from the group consisting of C, N, O, S, Si or P;
W is on each occurrence, identically or differently, CR, N, CR=CR or CR=N if Q stands for N, with the proviso that W stands for CR=CR or CR=N if Y stands for CR=CR or for CR=N; or W is NR if Q stands for C;
Z is C if W in this ligand stands for CR=CR or CR=N; or one Z stands for C and the other Z stands for N if W in this ligand stands for CR or N or NR;
R is on each occurrence, identically or differently, H, D, F, Cl, Br, I, $N(R^1)_2$, CN, $NO_2$, OH, COOH, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which may be substituted by one or more radicals $R^1$, where one or more non-adjacent $CH_2$ groups may be replaced by $R^1C=CR^1$, $C≡C$, $Si(R^1)_2$, C=O, $NR^1$, O, S or $CONR^1$ and where one or more H atoms may be replaced by D, F, Cl, Br, I or CN, or an aromatic or heteroaromatic ring system having 5 to 60 aromatic ring atoms, which may in each case be substituted by one or more radicals $R^1$, or an aryloxy or heteroaryloxy group having 5 to 40 aromatic ring atoms, which may be substituted by one or more radicals $R^1$, or an aralkyl or heteroaralkyl group having 5 to 40 aromatic ring atoms, which may be substituted by one or more radicals $R^1$, or a diarylamino group, diheteroarylamino group or arylheteroarylamino group having 10 to 40 aromatic ring atoms, which may be substituted by one or more radicals $R^1$; two adjacent radicals R here may also form a mono- or polycyclic, aliphatic, aromatic or heteroaromatic ring system with one another;
$R^1$ is on each occurrence, identically or differently, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which may be substituted by one or more radicals $R^2$, where one or more non-adjacent $CH_2$ groups may be replaced by $R^2C=CR^2$, $C≡C$, $Si(R^2)_2$, C=O, $NR^2$, O, S or $CONR^2$ and where one or more H atoms may be replaced by D, F, Cl, Br, I, CN or NO$_2$, or an aromatic or heteroaromatic ring system having 5 to 60 aromatic ring atoms, which may in each case be substituted by one or more radicals R$^2$, or an aryloxy or heteroaryloxy group having 5 to 40 aromatic ring atoms, which may be substituted by one or more radicals R$^2$, or an aralkyl or heteroaralkyl group having 5 to 40 aromatic ring atoms, which may be substituted by one or more radicals R$^2$, or a diarylamino group, diheteroarylamino group or arylheteroarylamino group having 10 to 40 aromatic ring atoms, which may be substituted by one or more radicals R$^2$; two or more adjacent radicals R$^2$ here may form a mono- or polycyclic, aliphatic ring system with one another;

R$^2$ is on each occurrence, identically or differently, H, D, F or an aliphatic, aromatic and/or heteroaromatic hydrocarbon radical having 1 to 20 C atoms, in which, in addition, one or more H atoms may be replaced by F; two or more substituents R$^2$ here may also form a mono- or polycyclic, aliphatic ring system with one another;

L' is, identically or differently on each occurrence, any desired co-ligand;

A is a counterion;

n is 1, 2 or 3;

m is 0, 1, 2, 3 or 4;

w is 1, 2 or 3;

x, y, z are on each occurrence, identically or differently, 0, 1, 2 or 3; where (w·x)=(y·z);

a plurality of ligands L here may also be linked to one another or L may be linked to L' via any desired bridge V and thus form a tridentate, tetradentate, pentadentate or hexadentate ligand system;

furthermore, a substituent R may also additionally coordinate to the metal,

A BRIEF DESCRIPTION OF THE FIGURES

A DETAILED DESCRIPTION OF THE PREFERRED EMBODIMENTS

Figure 1:
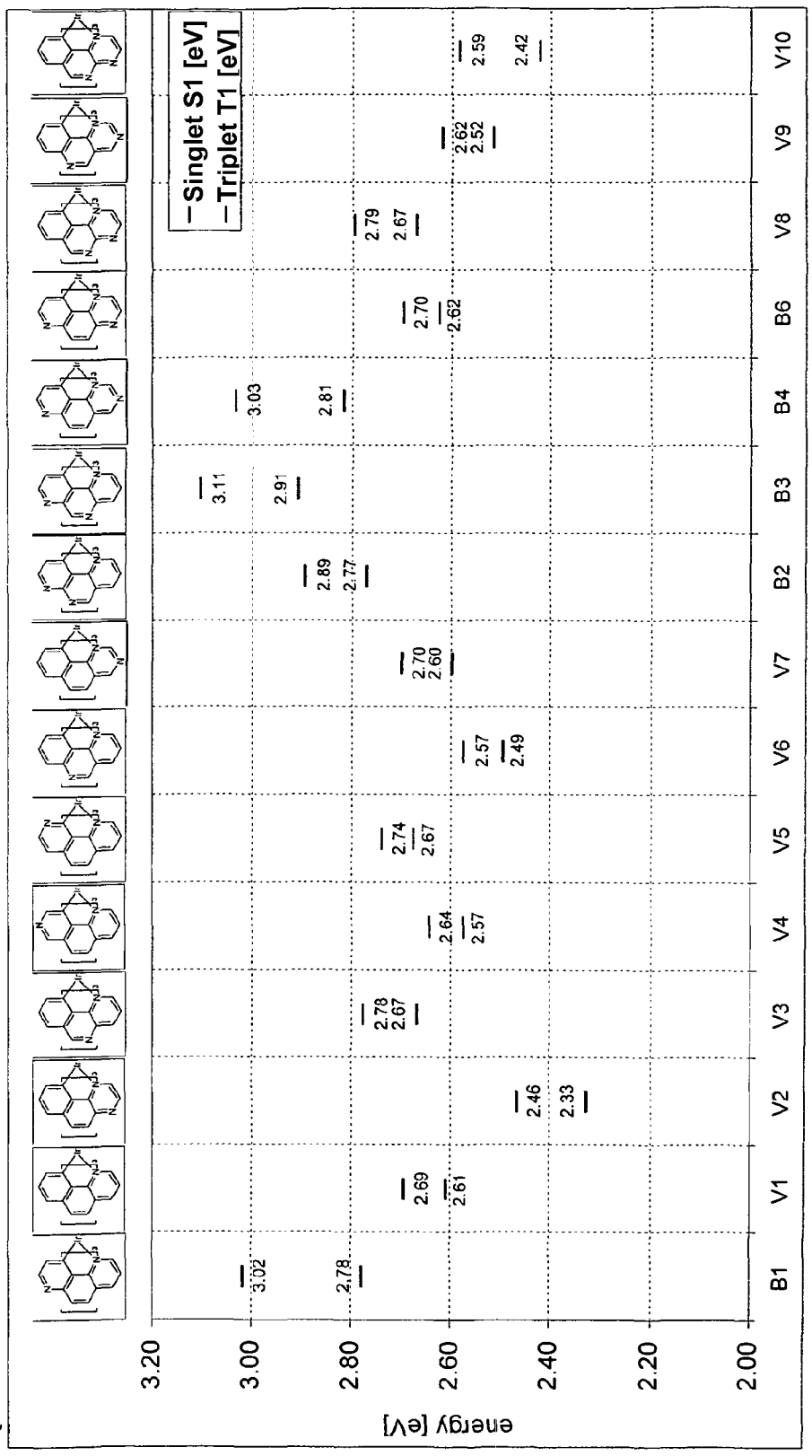
FIG. 1 shows the T1 and S1 level of various metal complexes, where the bridge —Y— is equal to —HC=CH— and the carbon atoms in the ligand have been replaced by 0, 1 or 2 N atoms.

Surprisingly, it has been found that the presence of the nitrogen atom in the six-membered ring in the para-position to the coordination to the metal in the moiety of the formula (2) is essential to the invention. Compared with analogous complexes which contain a carbon atom instead of the nitrogen atom at this position, the complexes according to the invention exhibit a significantly higher triplet level, so that the emission colour is shifted significantly towards blue.

The circle drawn in in the five-membered ring indicates, as generally conventional in organic chemistry, an aromatic or heteroaromatic ring having 6 π electrons.

The counterion A is has the opposite charge to the complex [M(L)$_n$(L')$_m$].

In the complexes of the formula (1), the indices n and m are selected so that the coordination number on the metal M corresponds in total, depending on the metal, to the usual coordination number for this metal. For transition metals, this is usually the coordination number 4, 5 or 6, depending on the metal. It is generally known that metal coordination compounds have different coordination numbers, i.e. a different number of ligands are bonded, depending on the metal and on the oxidation state of the metal. Since the preferred coordination numbers of metals or metal ions in different oxidation states belong to the general expert knowledge of the person skilled in the art in the area of organometallic chemistry or coordination chemistry, it is straightforward for the person skilled in the art to use a suitable number of ligands and thus to select the indices n and m suitably, depending on the metal and its oxidation state and depending on the precise structure of the ligand L.

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

An aromatic ring system in the sense of this invention contains 6 to 60 C atoms in the ring system. A heteroaromatic ring system in the sense of this invention contains 1 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for exampie, a C, N or O atom or a carbonyl group. Thus, for example, systems such as 9,9'-spirobifluorene, 9,9-diarylfluorene, triarylamine, diaryl ether, stilbene, etc., are also intended to be taken to be aromatic ring systems for the purposes of this invention, as are systems in which two or more aryl groups are interrupted, for example, by a linear or cyclic alkyl group or by a silyl group. Furthermore, systems in which two or more aryl or heteroaryl groups are bonded directly to one another, such as, for example, biphenyl or terphenyl, are likewise intended to be taken to be an aromatic or heteroaromatic ring system.

A cyclic alkyl, alkoxy or thioalkoxy group in the sense of this invention is taken to mean a monocyclic, bicyclic or polycyclic group.

For the purposes of the present invention, a C$_1$- to C$_{40}$-alkyl group, in which, in addition, individual H atoms or CH$_2$ groups may be substituted by the above-mentioned groups, is taken to mean, for example, the radicals methyl, ethyl, n-propyl, i-propyl, n-butyl, i-butyl, s-butyl, t-butyl, 2-methylbutyl, n-pentyl, s-pentyl, tert-pentyl, 2-pentyl, neopentyl, cyclopentyl, n-hexyl, s-hexyl, tert-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo-[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl or 2,2,2-trifluoroethyl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, sbutoxy, t-butoxy or 2-methylbutoxy.

An aromatic or heteroaromatic ring system having 5-60 aromatic ring atoms, which may also in each case be substituted by the radicals R mentioned above and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or transindenofluorene, cis- or trans-monobenzoindenofluorene, cis- or transdibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

If the compounds of the formula (1) are used in an organic electroluminescent device, it is preferred for the complexes to be uncharged, i.e. electrically neutral. This is achieved in a simple manner by selecting the charge of the ligands L and L' in such a way that they compensate for the charge of the complexed metal atom M. In this case, the index x=0, and the counterion A is not present.

If the compounds of the formula (1) are used in an organic electrochemical device, in particular in an organic light-emitting electrochemical cell, it is preferred for the complexes to be charged, i.e. for x not to be equal to 0. This is achieved in a simple manner by selecting the charge of the ligands L and L' in such a way that they do not compensate for the charge of the complexed metal ion M. In this case, at least one counterion A is present.

Preference is furthermore given to compounds of the formula (1), characterised in that the sum of the valence electrons around the metal atom is 16 in tetracoordinated complexes, 16 or 18 in pentacoordinated complexes and 18 in hexacoordinated complexes. This preference is due to the particular stability of these metal complexes.

Preference is given to compounds of the formula (1) in which M stands for a transition metal, where lanthanides and actinides are excluded, in particular for a tetracoordinated, pentacoordinated or hexacoordinated transition metal, particularly preferably selected from the group consisting of chromium, molybdenum, tungsten, rhenium, ruthenium, osmium, rhodium, iridium, nickel, palladium, platinum, copper, silver and gold, in particular molybdenum, tungsten, rhenium, ruthenium, osmium, iridium, copper, platinum and gold. Very particular preference is given to iridium and platinum. The metals here may be present in various oxidation states. The above-mentioned metals are preferably in the oxidation states Cr(0), Cr(II), Cr(III), Cr(IV), Cr(VI), Mo(0), Mo(II), Mo(III), Mo(1V), Mo(VI), W(0), W(II), W(III), W(IV), W(VI), Re(I), Re(II), Re(III), Re(IV), Ru(II), Ru(III), Os(II), Os(III), Os(IV), Rh(I), Rh(III), Ir(I), Ir(III), Ir(IV), Ni(0), Ni(II), Ni(IV), Pd(II), Pt(II), Pt(IV), Cu(I), Cu(II), Cu(III), Ag(I), Ag(II), Au(I), Au(III) and Au(V).

Particular preference is given to Mo(0), W(0), Re(I), Ru(II), Os(II), Rh(III), Cu(I), Ir(III) and Pt(II). Very particular preference is given to Ir(III) and Pt(II).

In a preferred embodiment of the invention, M is a tetracoordinated metal, and the index n stands for 1 or 2. If the index n=1, one bidentate or two monodentate ligands L', preferably one bidentate ligand L', are also coordinated to the metal M. If the index n=2, the index m=0. A preferred tetracoordinated metal is Pt(II).

In a further preferred embodiment of the invention, M is a hexacoordinated metal, and the index n stands for 1, 2 or 3, preferably for 2 or 3. If the index n=1, four monodentate or two bidentate or one bidentate and two monodentate or one tridentate and one monodentate or one tetradentate ligand L', preferably two bidentate ligands L', are also coordinated to the metal. If the index n=2, one bidentate or two monodentate ligands L', preferably one bidentate ligand L', are also coordinated to the metal. If the index n=3, the index m=0. A preferred hexacoordinated metal is Ir(III).

As described above, the bridging group Y is a diatomic bridge containing two bridge atoms, which are selected, identically or differently on each occurrence, from the group consisting of C, N, O, S, Si and P, where these bridge atoms may be substituted or unsubstituted. In a preferred embodiment of the invention, at least one of the two bridge atoms is a carbon atom. In a particularly preferred embodiment of the invention, one of the two bridge atoms is a carbon atom and the other bridge atom is selected from C, N or O. These atoms may be substituted by radicals R. The carbon atom can be a group $CR_2$ or a carbonyl group. Furthermore, the group Y may also be a group —RC═CR— or —RC═N— or an aromatic or heteroaromatic group which is bonded via two carbon atoms or via one carbon atom and one nitrogen atom.

Preferred bridges Y are selected from the following structures: —CR═CR—, —CR═N—, —C(═O)—$CR_2$—, —C(═O)—NR—, —C(═O)—O— and —$CR_2$—$CR_2$— and from the structures of the following formulae (A) to (E), formula (A)

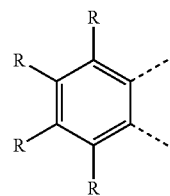

-continued

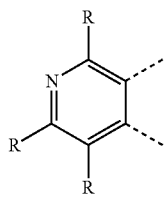
formula (B)

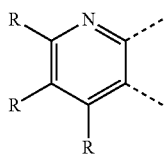
formula (C)

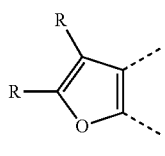
formula (D)

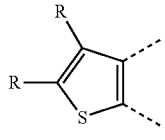
formula (E)

where R has the meaning given above and the dashed bonds in each case indicate the bonding of this group in the corresponding ligand.

Asymmetrical bridges Y may in accordance with the invention be bonded in the two possible orientations. This is explained diagrammatically below for the example of Y=—C(=O)—O—:

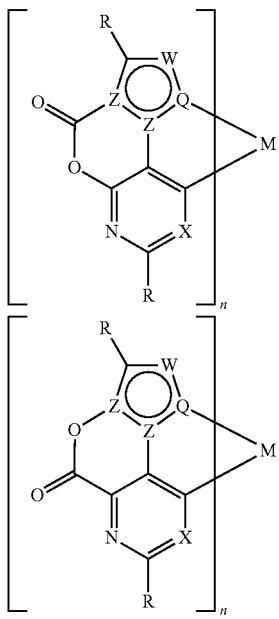

The group —C(=O)—O— may on the one hand be bonded in such a way that the carbonyl group is bonded to the group Z and the oxygen atom is bonded to the six-membered ring (1st structure). However, the group —C(=O)—O— may on the other hand also be bonded in such a way that the carbonyl group is bonded to the six-membered ring and the oxygen atom is bonded to the group Z (2nd structure). Both embodiments are in accordance with the invention.

If Q stands for C, it is preferably a carbene which is coordinated to the metal M. As defined above, the group W in the case stands for NR. If Q stands for C, W preferably stands for NR and the group Z, which is bonded directly to Q, stands for N.

In a preferred embodiment of the invention, Q stands for N.

The upper part-ring of the ligand L may, depending on the choice of the group W, stand for a five-membered ring or a six-membered ring.

If the upper part-ring stands for a five-membered ring, preferred embodiment of the moieties of the formula (2) are the structures of the following formulae (3) to (7),

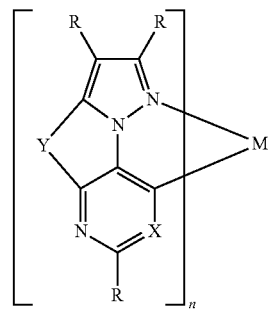
formula (3)

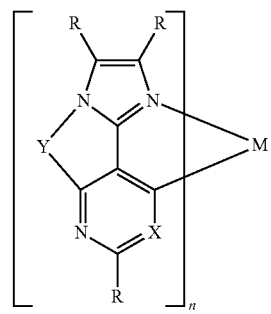
formula (4)

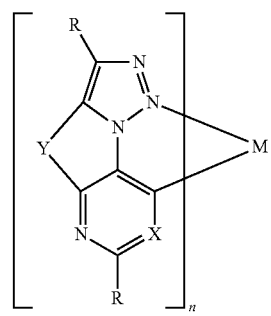
formula (5)

formula (6)

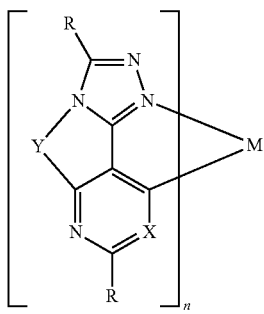

formula (7)

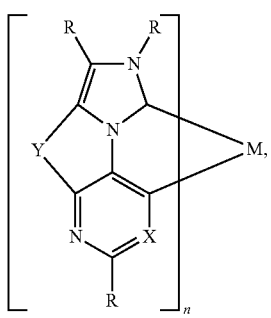

where the symbols and indices used have the meanings given above.

Particular preference is given to structures of the formula (3) and (4).

If the upper part-ring stands for a six-membered ring, preferred embodiment of the moieties of the formula (2) are the structures of the following formulae (8) to (10), formula (8)

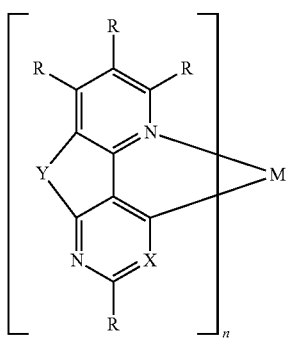

formula (9)

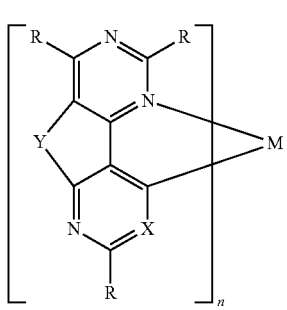

formula (10)

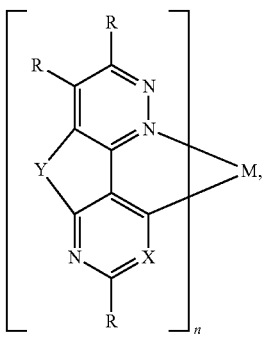

where the symbols and indices used have the meanings given above.

Particular preference is given to the structures of the formula (8) and (9), very particularly preferably the structures of the formula (8).

In a further preferred embodiment of the invention, X in the moiety of the formula (2) and in the moieties of the formulae (3) to (10) stands for CR, in particular for CH.

In a particularly preferred embodiment of the invention, the preferences given above occur simultaneously.

The radicals R in the moiety of the formula (2) are preferably selected on each occurrence, identically or differently, from the group consisting of H, D, F, Br, I, $N(R^1)_2$, CN, $Si(R^1)_3$, $B(OR^1)_2$, $C(=O)R^1$, a straight-chain alkyl group having 1 to 10 C atoms or an alkenyl group having 2 to 10 C atoms or a branched or cyclic alkyl group having 3 to 10 C atoms, each of which may be substituted by one or more radicals $R^1$; where one or more H atoms may be replaced by D or F, or an aromatic or heteroaromatic ring system having 5 to 30 aromatic ring atoms, which may in each case be substituted by one or more radicals $R^1$; two adjacent radical R here may also form a mono- or polycyclic, aliphatic, aromatic or heteroaromatic ring system with one another. These radicals R are particularly preferably selected on each occurrence, identically or differently, from the group consisting of H, D, F, $N(R^1)_2$, a straight-chain alkyl group having 1 to 6 C atoms or a branched or cyclic alkyl group having 3 to 10 C atoms, where one or more H atoms may be replaced by D or F, or an aromatic or heteroaromatic ring system having 5 to 24 aromatic ring atoms, which may in each case be substituted by one or more radicals $R^1$; two adjacent radical R here may also form a mono- or polycyclic, aliphatic, aromatic or heteroaromatic ring system with one another.

It is furthermore possible for the substituent R which is in ortho-position to the metal coordination to represent a coordinating group which is likewise coordinated or bonded to the metal M. Preferred coordinating groups R are aryl or heteroaryl groups, for example phenyl or pyridyl, aryl or alkyl cyanides, aryl or alkyl isocyanides, amines or amides, alcohols or alcoholates, thioalcohols or thioalcoholates, phosphines, phosphites, carbonyl functions, carboxylates, carbamides or aryl- or alkylacetylides. The moieties ML of the following formulae (11) to (16), for example, are accessible here:

formula (11)

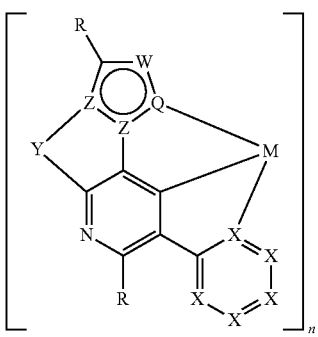

formula (12)

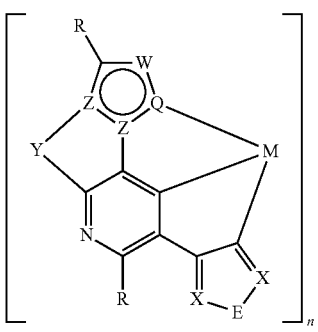

formula (13)

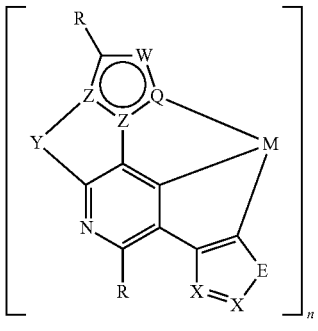

formula (14)

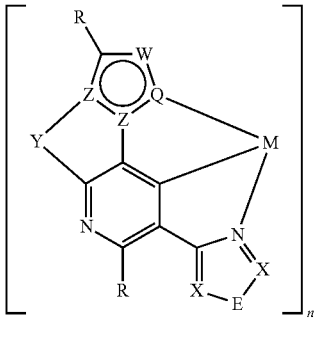

formula (15)

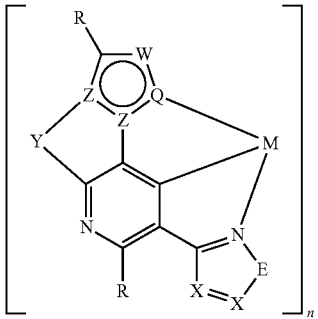

formula (16)

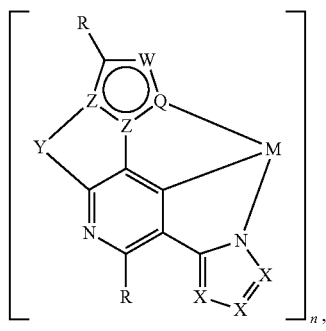

where the symbols and indices have the same meanings as described above, where the coordinating group X in formula (11) stands for C or N, and W stands, identically or differently on each occurrence, for S, O or $NR^1$.

Formulae (11) to (16) show, merely by way of example, how the substituent R can additionally coordinate to the metal. Other groups R which coordinate to the metal are also accessible entirely analogously without further inventive step. For example, it is possible, entrely analogously, for the group W in the ligand L to stand for CR and for this substituent R to be bonded to M, for example via the same aryl or heteroaryl groups as indicated in the formulae (11) to (16).

As described above, a bridging unit V which links this ligand L to one or more further ligands L or L' may also be present instead of one of the radicals R. In a preferred embodiment of the invention, this bridging unit V is bonded in the ortho- or meta-position to the coordinating atom. The ligand consequently has a tridentate or polydentate or polypodal character. It is also possible for two such bridging units V to be present. This results in the formation of macrocyclic ligands or in the formation of cryptates.

Preferred structures containing polydentate ligands are the metal complexes of the following formulae (17) to (22), formula (17)

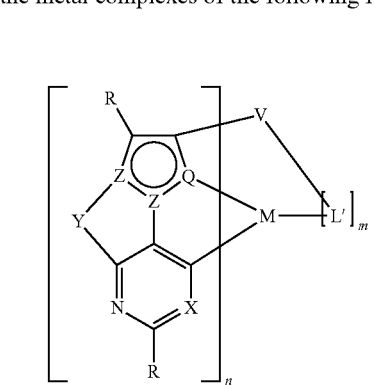

formula (18)

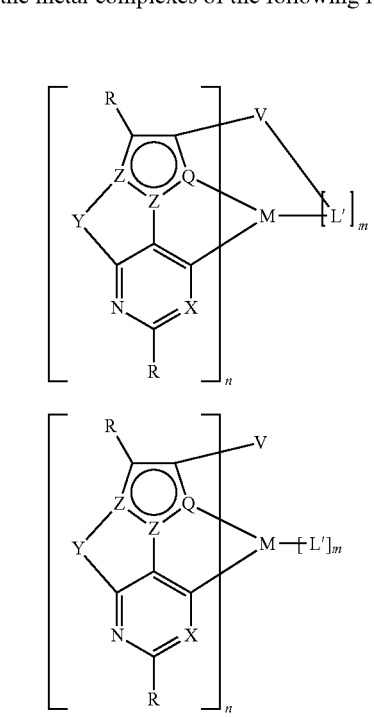

-continued

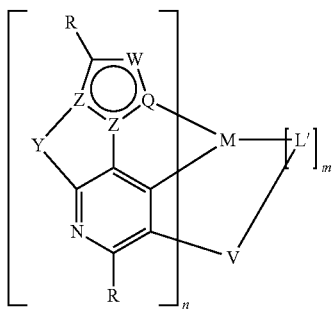

formula (19)

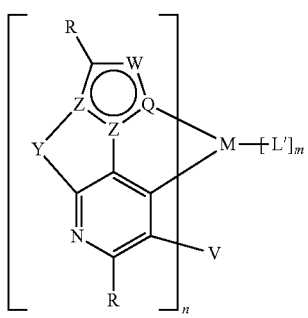

formula (20)

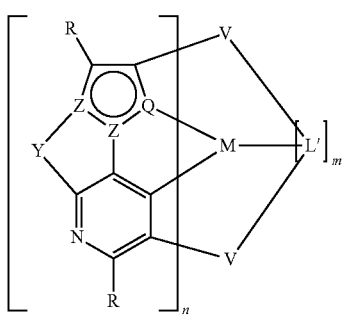

formula (21)

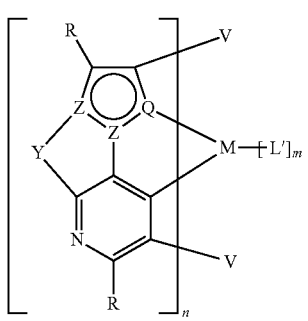

formula (22)

where the symbols used have the above-mentioned meanings, where V preferably represents a bridging unit containing 1 to 80 atoms from the third, fourth, fifth and/or sixth main group (IUPAC group 13, 14, 15 or 16) or a 3- to 6-membered homo- or heterocycle which covalently bonds the part-ligands L to one another or covalently bonds L to L'. The bridging unit V here may also have an asymmetrical structure, i.e. the linking of V to L and L' need not be identical. The bridging unit V can be neutral, singly, doubly or triply negatively charged or singly, doubly or triply positively charged. V is preferably neutral or singly negatively charged or singly positively charged, particularly preferably neutral. The preferences mentioned above for the moiety $ML_n$ apply to the ligands, and n is preferably at least 2.

The precise structure and chemical composition of the group V does not have a significant effect on the electronic properties of the complex since the job of this group is essentially to increase the chemical and thermal stability of the complexes by bridging L to one another or to L'.

If V is a trivalent group, i.e. bridges three ligands L to one another or two ligands L to L' or one ligand L to two ligands L', V is preferably selected, identically or differently on each occurrence, from the group consisting of B, $B(R^1)^-$, $B(C(R^1)_2)_3$, $(R^1)B(C(R^1)_2)_3^-$, $B(O)_3$, $(R^1)B(O)_3^-$, $B(C(R^1)_2C(R^1)_2)_3$, $(R^1)B(C(R^1)_2C(R^1)_2)_3$, $B(C(R^1)_2O)_3^-$, $(R^1)B(C(R^1)_2O)_3^-$, $B(OC(R^1)_2)_3$, $(R^1)B(OC(R^1)_2)_3^-$, $C(R^1)$, $CO^-$, $CN(R^1)_2$, $(R^1)C(C(R^1)_2)_3$, $(R^1)C(O)_3$, $(R^1)C(C(R^1)_2C(R^1)_2)_3$, $(R^1)C(C(R^1)_2O)_3$, $(R^1)C(OC(R^1)_2)_3$, $(R^1)C(Si(R^1)_2)_3$, $(R^1)C(Si(R^1)_2C(R^1)_2)_3$, $(R^1)C(C(R^1)_2Si(R^1)_2)_3$, $(R^1)C(Si(R^1)_2Si(R^1)_2)_3$, $Si(R^1)$, $(R^1)Si(C(R^1)_2)_3$, $(R^1)Si(O)_3$, $(R^1)Si(C(R^1)_2C(R^1)_2)_3$, $(R^1)Si(OC(R^1)_2)_3$, $(R^1)Si(C(R^1)_2O)_3$, $(R^1)Si(Si(R^1)_2)_3$, $(R^1)Si(Si(R^1)_2C(R^1)_2)_3$, $(R^1)Si(C(R^1)_2Si(R^1)_2)_3$, $(R^1)Si(Si(R^1)_2Si(R^1)_2)_3$, N, NO, $N(R^1)^+$, $N(C(R^1)_2)_3$, $(R^1)N(C(R^1)_2)_3^+$, $N(C=O)_3$, $N(C(R^1)_2C(R^1)_2)_3$, $(R^1)N(C(R^1)_2C(R^1)_2)_3^+$, P, $P(R^1)^+$, PO, PS, $P(O)_3$, $PO(O)_3$, $P(OC(R^1)_2)_3$, $PO(OC(R^1)_2)_3$, $P(C(R^1)_2)_3$, $P(R^1)(C(R^1)_2)_3^+$, $PO(C(R^1)_2)_3$, $P(C(R^1)_2C(R^2)_2)_3$, $P(R^1)(C(R^1)_2C(R^1)_2)_3^+$, $PO(C(R^1)_2C(R^1)_2)_3$, $S^+$, $S(C(R^1)_2)_3^+$, $S(C(R^1)_2C(R^1)_2)_3^+$, or a unit of the formula (23), (24), (25) or (26),

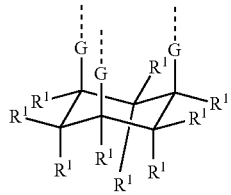

formula (23)

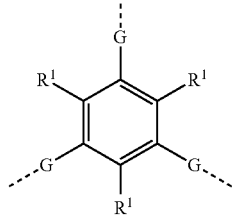

formula (24)

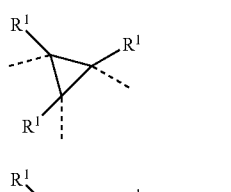

formula (25)

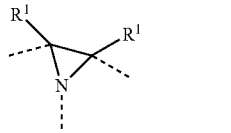

formula (26)

where the dashed bonds in each case indicate the bond to the part-ligands L or L', and G is selected, identically or differently on each occurrence, from the group consisting of a single bond, O, S, S(=O), $S(=O)_2$, $NR^1$, $PR^1$, $P(=O)R^1$, $P(=NR^1)$, $C(R^1)_2$, C(=O), $C(=NR^1)$, $C(=C(R^1)_2)$, $Si(R^1)_2$ or $BR^1$. The other symbols used have the meanings given above.

If V is a divalent group, i.e. bridges two ligands L to one another or one ligand L to L', V is preferably selected, identically or differently on each occurrence, from the group consisting of aus $BR^1$, $B(R^1)_2^-$, $C(R^1)_2$, $C(=O)$, $Si(R^1)_2$, $NR^1$, $PR^1$, $P(R^1)_2^+$, $P(=O)(R^1)$, $P(=S)(R^1)$, O, S, Se, or a unit of the formulae (27) to (35), formula (27)
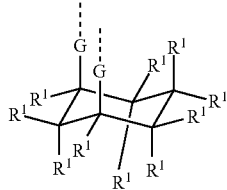

formula (28)
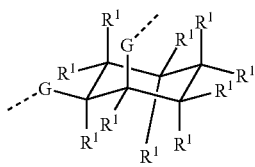

formula (29)
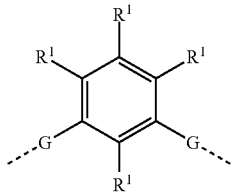

formula (30)
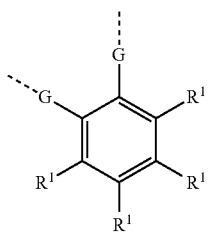

formula (31)
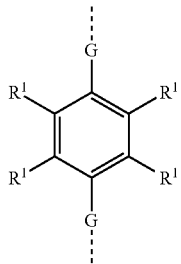

formula (32)
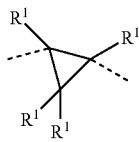

formula (33)
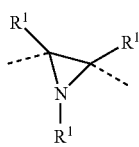

formula (34)
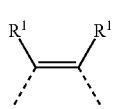

formula (35)
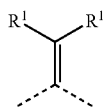

where the dashed bonds in each case indicate the bond to the part-ligands L or L' and the symbols used each have the meanings indicated above.

Preferred ligands L' as occur in formula (1) are described below. The ligand groups L' can also be selected correspondingly if they are bonded to L via a bridging unit V, as indicated in formulae (17) to (22).

The ligands L' are preferably neutral, monoanionic, dianionic or trianionic ligands, particularly preferably neutral or monoanionic ligands. They can be monodentate, bidentate, tridentate or tetradentate and are preferably bidentate, i.e. preferably have two coordination sites. As described above, the ligands L' can also be bonded to L via a bridging group V.

Preferred neutral, monodentate ligands L' are selected from the group consisting of carbon monoxide, nitrogen monoxide, alkyl cyanides, such as, for example, acetonitrile, aryl cyanides, such as, for example, benzonitrile, alkyl isocyanides, such as, for example, methyl isonitrile, aryl isocyanides, such as, for example, benzoisonitrile, amines, such as, for example, trimethylamine, triethylamine, morpholine, phosphines, in particular halophosphines, trialkylphosphines, triarylphosphines or alkylarylphosphines, such as, for example, trifluorophosphine, trimethylphosphine, tricyclohexylphosphine, tri-tert-butylphosphine, triphenylphosphine, tris(pentafluorophenyl)phosphine, dimethylphenylphosphine, methyldiphenylphosphine, bis(tert-butyl)phenylphosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsine, tris(pentafluorophenyl)arsine, stibines, such as, for example, trifluorostibine, trimethylstibine, tricyclohexylstibine, tri-tert-butylstibine, triphenylstibine, tris(pentafluorophenyl)stibine, nitrogen-containing heterocycles, such as, for example, pyridine, pyridazine, pyrazine, pyrimidine, triazine, and carbenes, in particular Arduengo carbenes.

Preferred monoanionic, monodentate ligands L' are selected from hydride, deuteride, the halides $F^-$, $Cl^-$, $Br^-$ and $I^-$, alkylacetylides, such as, for example, methyl-C≡C$^-$, tert-butyl-C≡C$^-$, arylacetylides, such as, for example, phenyl-C≡C$^-$, cyanide, cyanate, isocyanate, thiocyanate, isothiocyanate, aliphatic or aromatic alcoholates, such as, for example, methanolate, ethanolate, propanolate, isopropanolate, tert-butylate, phenolate, aliphatic or aromatic thioalcoholates, such as, for example, methanethiolate, ethanethiolate, propanethiolate, isopropanethiolate, tert-thiobutylate, thiophenolate, amides, such as, for example, dimethylamide, diethylamide, diisopropylamide, morpholide, carboxylates, such as, for example, acetate, trifluoroacetate, propionate, benzoate, aryl groups, such as, for example, phenyl, naphthyl, and anionic, nitrogen-containing heterocycles, such as pyrrolide, imidazolide, pyrazolide. The alkyl groups in these groups are preferably $C_1$-$C_{20}$-alkyl groups, particularly preferably $C_1$-$C_{10}$-alkyl groups, very particularly preferably $C_1$-$C_4$-alkyl groups. An aryl group is also taken to mean heteroaryl groups. These groups are as defined above.

Preferred di- or trianionic ligands are $O^{2-}$, $S^{2-}$, carbides, which result in coordination in the form R—C≡M, and nitrenes, which result in coordination in the form R—N=M, where R generally stands for a substituent, or N³⁻.

Preferred neutral or mono- or dianionic, bidentate or polydentate ligands L' are selected from diamines, such as, for example, ethylenediamine, N,N,N',N'-tetramethylethylenediamine, propylenediamine, N,N,N',N'-tetramethylpropylenediamine, cis- or trans-diaminocyclohexane, cis- or transN,N,N',N'-tetramethyldiaminocyclohexane, imines, such as, for example, 2-[1-(phenylimino)ethyl]pyridine, 2-[1-(2-methylphenylimino)ethyl]pyridine, 2-[1-(2,6-diisopropylphenylimino)ethyl]pyridine, 2-[1-(methylimino) ethyl]-pyridine, 2-[1-(ethylimino)ethyl]pyridine, 2-[1-(isopropylimino)ethyl]pyridine, 2-[1-(tert-butylimino)ethyl] pyridine, diimines, such as, for example, 1,2-bis (methylimino)ethane, 1,2-bis(ethylimino)ethane, 1,2-bis (isopropylimino)ethane, 1,2-bis(tert-butylimino)ethane, 2,3-bis(methylimino)butane, 2,3-bis(ethylimino)butane, 2,3-bis(isopropylimino)butane, 2,3-bis(tert-butylimino)butane, 1,2-bis(phenylimino)ethane, 1,2-bis(2-methylphenylimino) ethane, 1,2-bis(2,6-diisopropylphenylimino)ethane, 1,2-bis (2,6-di-tert-butylphenylimino)ethane, 2,3-bis(phenylimino) butane, 2,3-bis(2-methylphenylimino)butane, 2,3-bis(2,6-diisopropylphenylimino)butane, 2,3-bis(2,6-di-tert-butylphenylimino)butane, heterocycles containing two nitrogen atoms, such as, for example, 2,2'-bipyridine, o-phenanthroline, diphosphines, such as, for example, bis (diphenylphosphino)methane, bis(diphenylphosphino)ethane, bis(diphenylphosphino)propane, bis(diphenylphosphino)butane, bis(dimethylphosphino)methane, bis (dimethylphosphino)ethane, bis(dimethylphosphino) propane, bis(diethylphosphino)methane, bis (diethylphosphino)ethane, bis(diethylphosphino)propane, bis(di-tert-butylphosphino)methane, bis(di-tert-butylphosphino)ethane, bis(tert-butylphosphino)propane, 1,3-diketonates derived from 1,3-diketones, such as, for example, acetylacetone, benzoylacetone, 1,5-diphenylacetylacetone, dibenzoylmethane, bis(1,1,1-trifluoroacetyl)methane, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol and dithiolates derived from dithiols, such as, for example, 1,2-ethylenedithiol, 1,3-propylenedithiol.

Preferred tridentate ligands are borates of nitrogen-containing heterocycles, such as, for example, tetrakis(1-imidazolyl) borate and tetrakis(1-pyrazolyl) borate.

Preference is furthermore given to bidentate monoanionic, neutral or dianionic ligands L', in particular monoanionic ligands, which, with the metal, form a cyclometallated five- or six-membered ring with at least one metal-carbon bond, in particular a cyclometallated five-membered ring. These are, in particular, ligands as are generally used in the area of phosphorescent metal complexes for organic electroluminescent devices, i.e. ligands of the type phenylpyridine, naphthylpyridine, phenylquinoline, phenylisoquinoline, etc., each of which may be substituted by one or more radicals R. A multiplicity of ligands of this type is known to the person skilled in the art in the area of phosphorescent electroluminescent devices, and he will be able, without inventive step, to select further ligands of this type as ligand L' for compounds of the formula (1). The combination of two groups as depicted by the following formulae (36) to (63) is generally particularly suitable for this purpose, where one group is preferably bonded via a neutral nitrogen atom or a carbene carbon atom and the other group is preferably bonded via a negatively charged carbon atom or a negatively charged nitrogen atom. The ligand L' can then be formed from the groups of the formulae (36) to (63) through these groups bonding to one another in each case at the position denoted by #. The position at which the groups coordinate to the metal is denoted by *. These groups may also be bonded to the ligand L via one or two bridging units V.

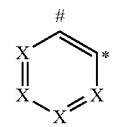

formula (36)

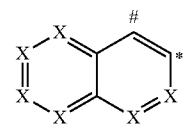

formula (37)

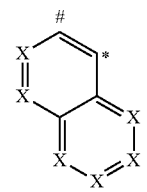

formula (38)

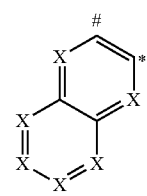

formula (39)

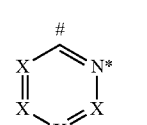

formula (40)

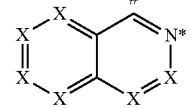

formula (41)

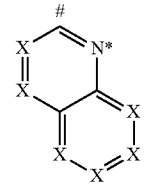

formula (42)

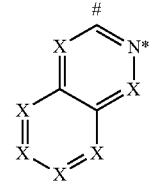

formula (43)

-continued

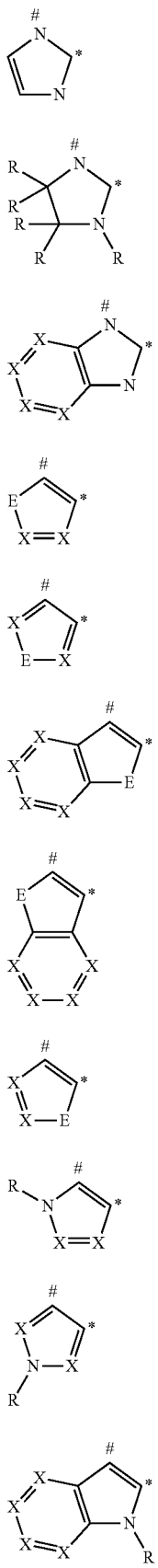

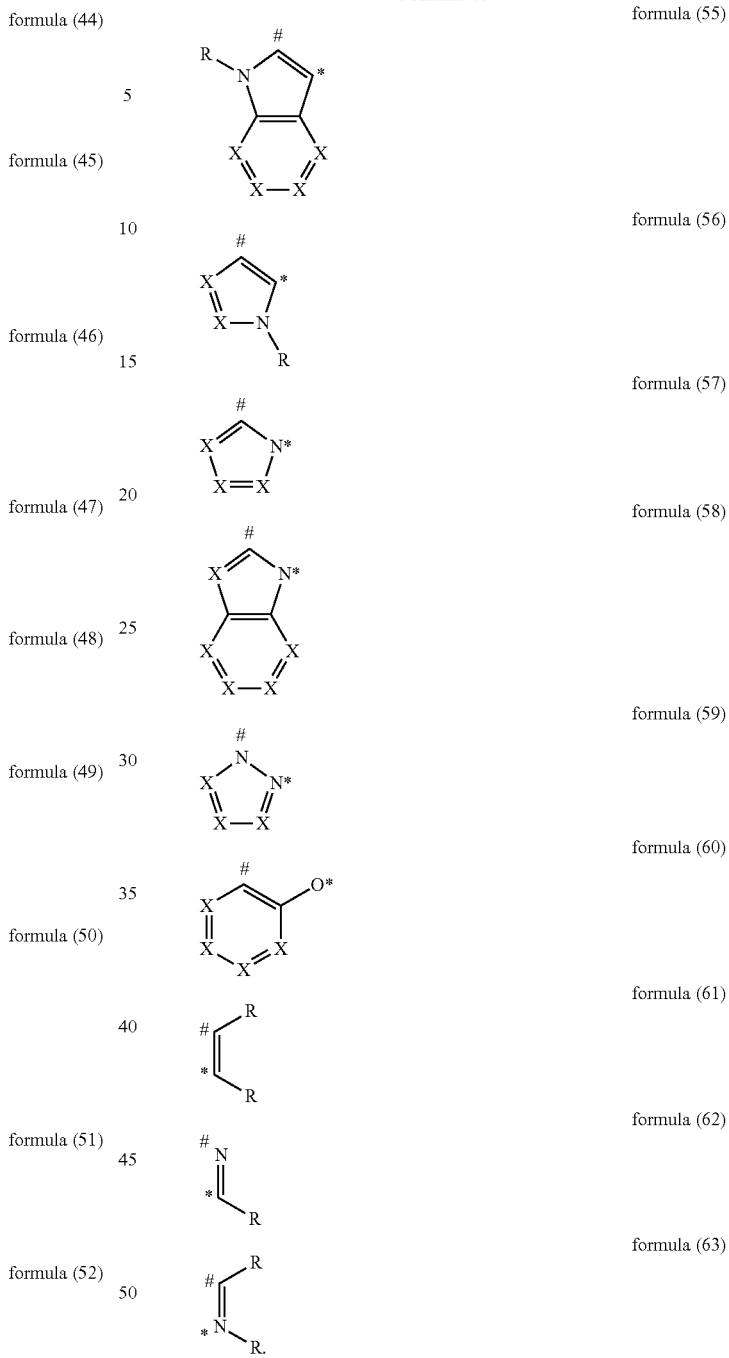

E here stands on each occurrence, identically or differently, for S or O. Furthermore, X stands on each occurrence, identically or differently, for CR or N, and R has the same meaning as described above. Preferably, a maximum of three symbols X in each group stand for N, particularly preferably a maximum of two symbols X in each group stand for N, very particularly preferably a maximum of one symbol X in each group stands for N. Especially preferably, all symbols X stand for CR.

Likewise preferred ligands L' are $\eta^5$-cyclopentadienyl, $\eta^5$-pentamethylcyclopentadienyl, $\eta^6$-benzene or $\eta^7$-cycloheptatrienyl, each of which may be substituted by one or more radicals R.

Preferred radicals R in the structures shown above are selected on each occurrence, identically or differently, from the group consisting of H, D, F, Br, N(R$^1$)$_2$, CN, B(OR$^1$)$_2$, C(=O)R$^1$, P(=O)(R$^1$)$_2$, a straight-chain alkyl group having 1 to 10 C atoms or a straight-chain alkenyl or alkynyl group having 2 to 10 C atoms or a branched or cyclic alkyl group having 3 to 10 C atoms, each of which may be substituted by one or more radicals R$^1$, where one or more H atoms may be replaced by D or F, or an aromatic or heteroaromatic ring system having 5 to 14 aromatic ring atoms, which may in each case be substituted by one or more radicals R$^1$; two or more adjacent radicals R here may also form a mono- or polycyclic, aliphatic, aromatic and/or benzo-fused ring system with one another. Particularly preferred radicals R are selected on each occurrence, identically or differently, from the group consisting of H, D, F, Br, CN, B(OR$^1$)$_2$, a straight-chain alkyl group having 1 to 5 C atoms, in particular methyl, or a branched or cyclic alkyl group having 3 to 5 C atoms, in particular isopropyl or tert-butyl, where one or more H atoms may be replaced by D or F, or an aromatic or heteroaromatic ring system having 5 to 12 aromatic ring atoms, which may in each case be substituted by one or more radicals R$^1$; two or more radicals R here may also form a mono- or polycyclic, aliphatic, aromatic and/or benzo-fused ring system with one another.

If the complexes are charged, the complex is combined with a counterion A. If the complex is positively charged, the counterions A are preferably selected from the group consisting of fluoride, chloride, bromide, iodide, hydroxide, tetrafluoroborate, hexafluorophosphate, sulfate, phosphate, nitrate, carbonate, alkylcarboxylate, where the alkyl group preferably has 1 to 20 C atoms, or arylcarboxylate. If the complex is negatively charged, the counterions A are preferably selected from the group consisting of lithium, sodium, potassium, ammonium, tetraalkylammonium or tetraalkylphosphonium, where the alkyl group in each case preferably has 1 to 10 C atoms.

The complexes according to the invention may be facial or pseudofacial, or they may be meridional or pseudomeridional.

The preferred embodiments indicated above can be combined with one another as desired. In a particularly preferred embodiment of the invention, the preferred embodiments indicated above apply simultaneously.

Examples of compounds of the formula (1) according to the invention are compounds (1) to (72) shown in the following table.

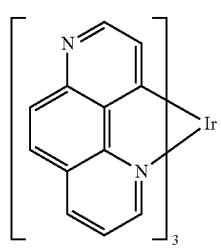
(1)

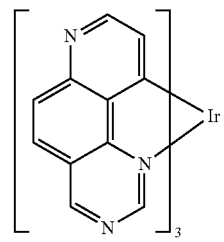
(2)

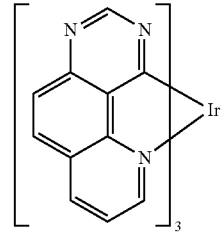
(3)

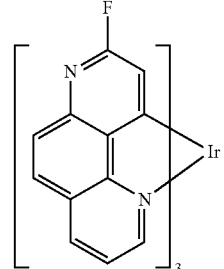
(4)

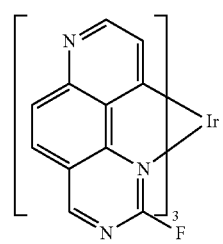
(5)

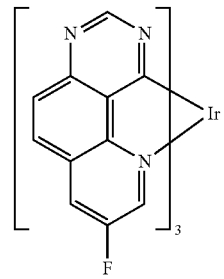
(6)

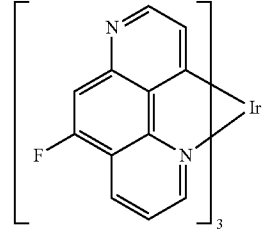
(7)

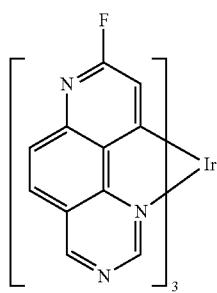
(8)
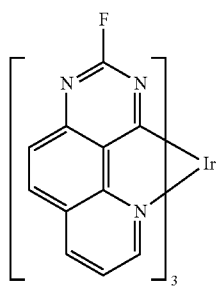
(9)
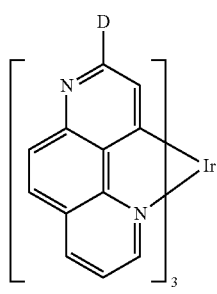
(10)
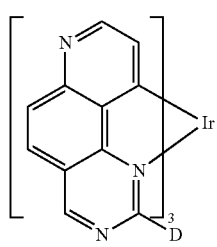
(11)
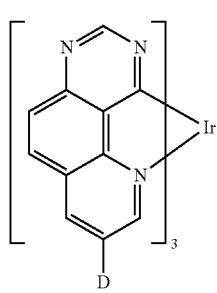
(12)

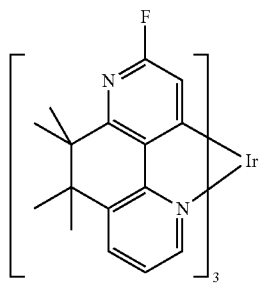 (19)
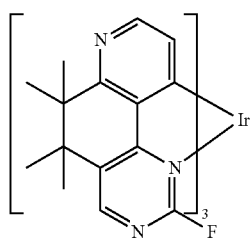 (20)
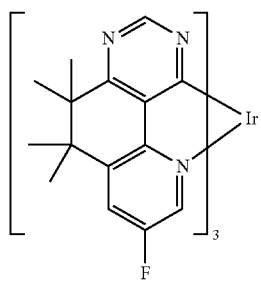 (21)
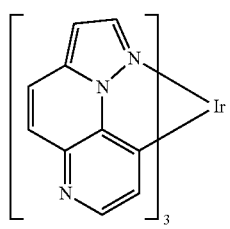 (22)
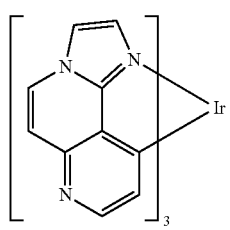 (23)
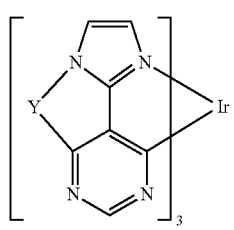 (24)
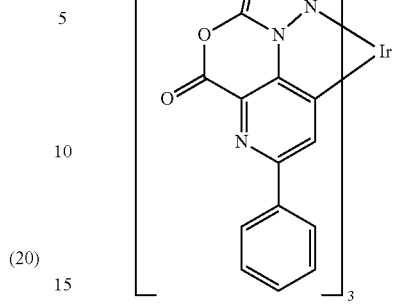 (25)
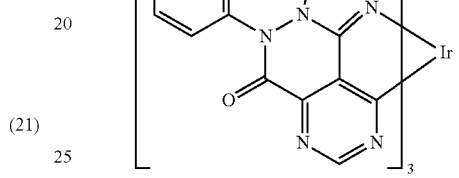 (26)
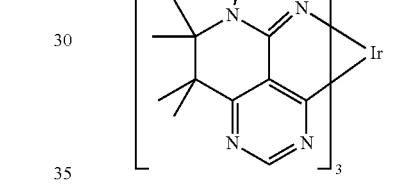 (27)
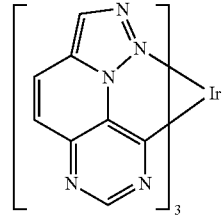 (28)
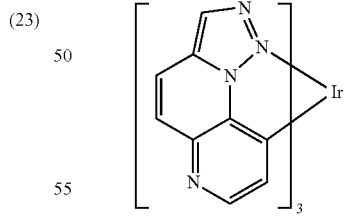 (29)
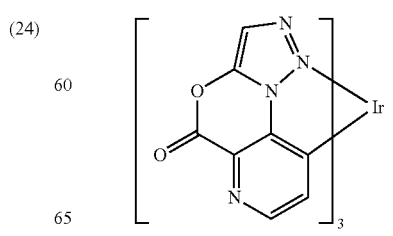 (30)

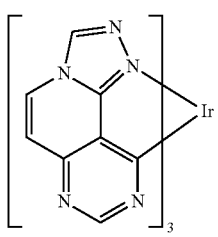
(31)
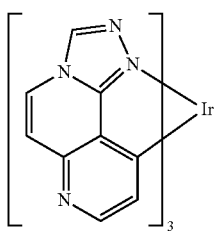
(32)
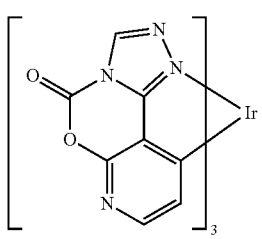
(33)
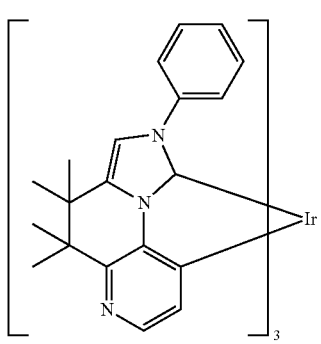
(34)
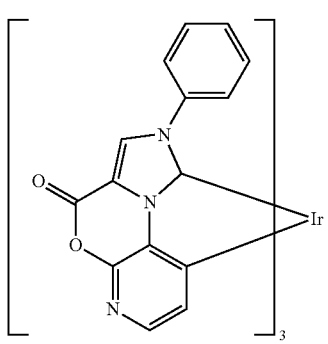
(35)
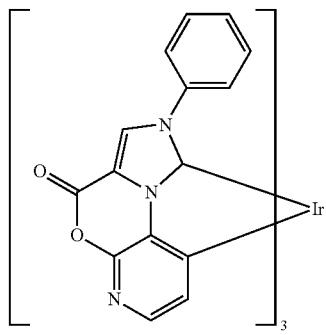
(36)
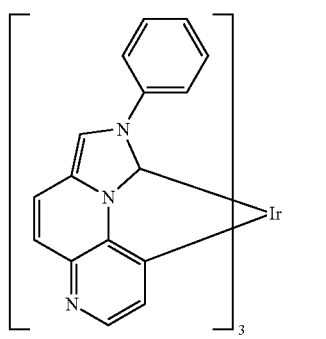
(37)
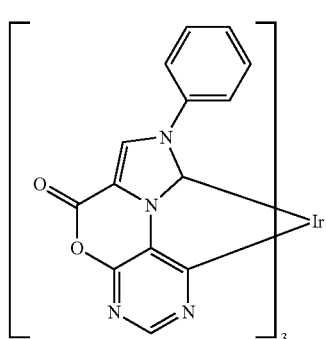
(38)
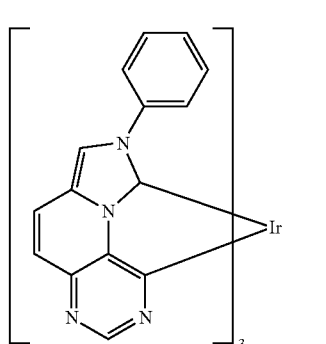
(39)
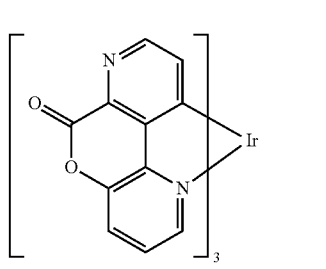
(40)

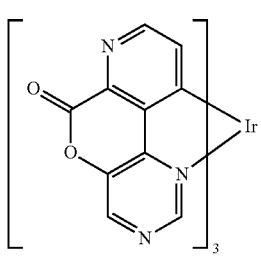 (41)
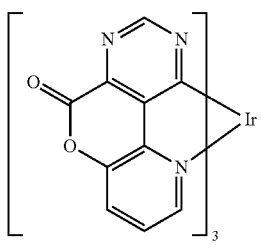 (42)
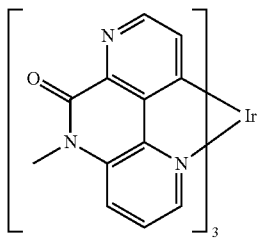 (43)
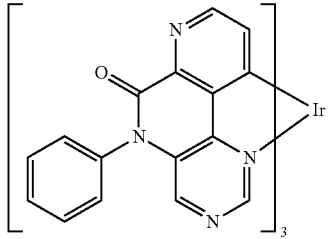 (44)
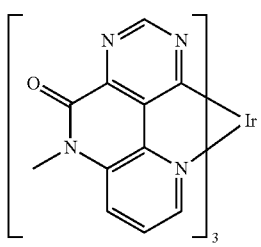 (45)
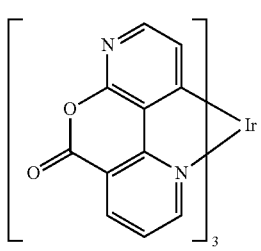 (46)
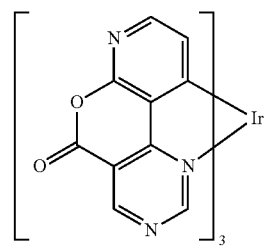 (47)
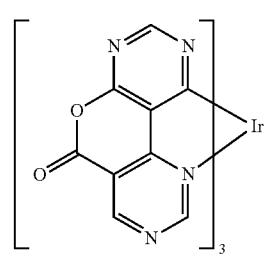 (48)
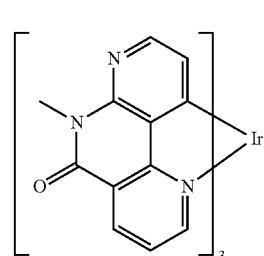 (49)
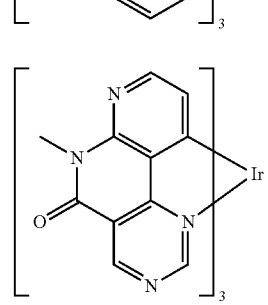 (50)
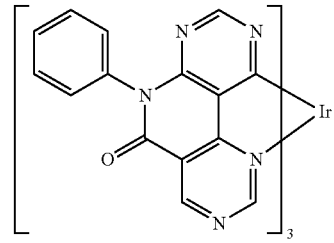 (51)
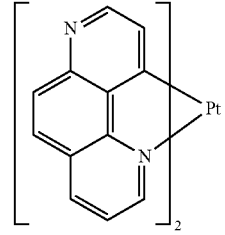 (52)

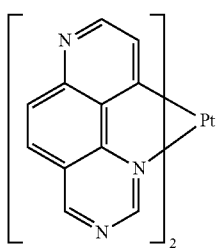
(53)
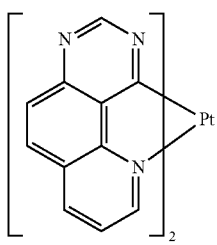
(54)
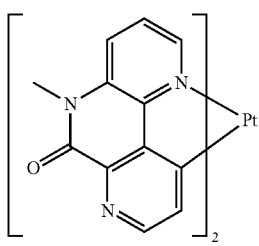
(55)
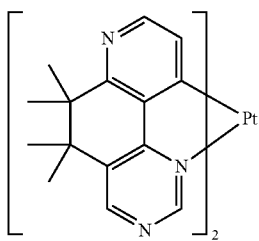
(56)
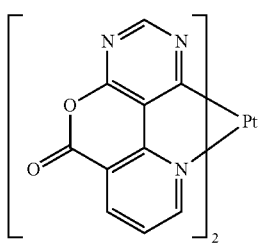
(57)
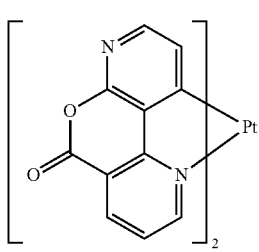
(58)
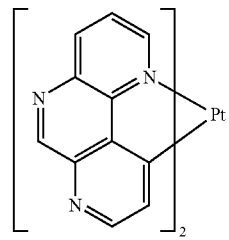
(59)
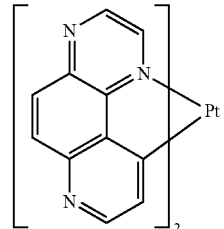
(60)
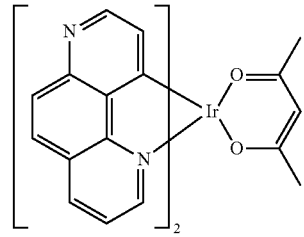
(61)
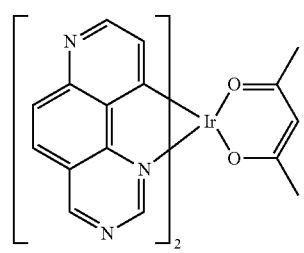
(62)
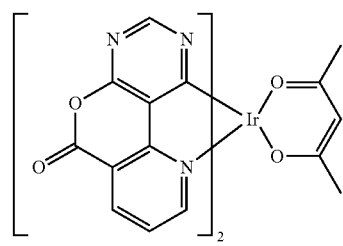
(63)
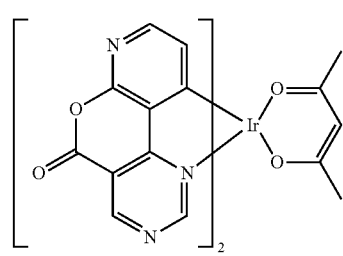
(64)

-continued

(65) 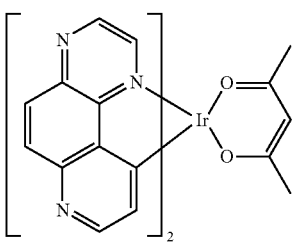

(66) 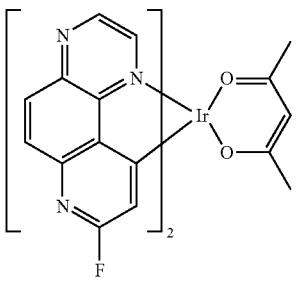

(67) 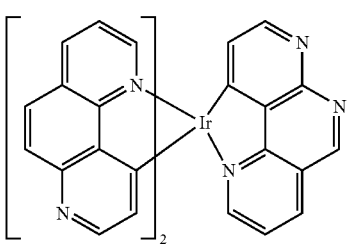

(68) 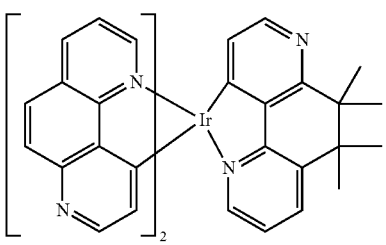

(69) 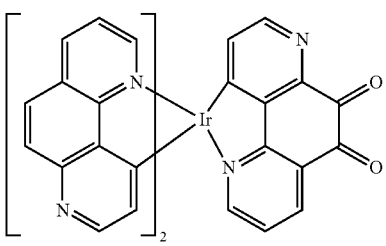

(70) 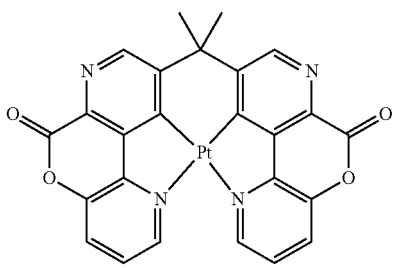

(71)

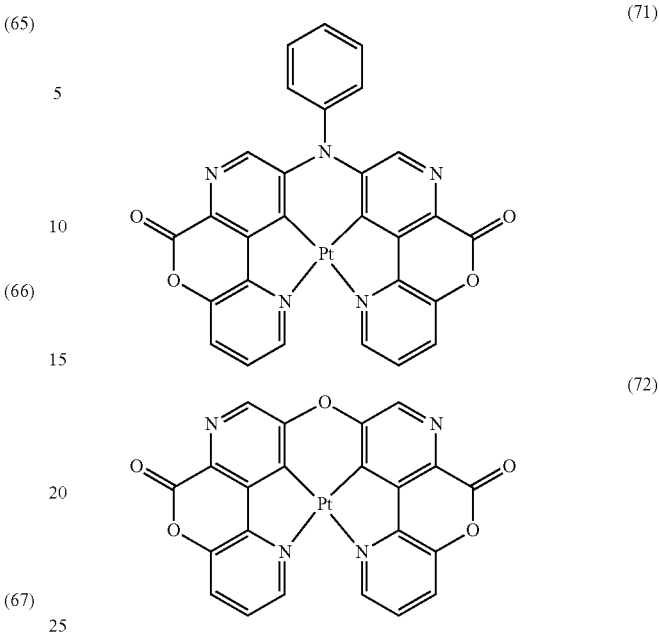

(72)

The metal complexes according to the invention can in principle be prepared by various processes. However, the processes described below have proven particularly suitable.

The present invention therefore furthermore relates to a process for the preparation of the metal complex compounds of the formula (1) by reaction of the corresponding free ligands with metal alkoxides of the formula (64), with metal ketoketonates of the formula (65), with metal halides of the formula (66) or with dimeric metal complexes of the formula (67), $$M(OR)_n \qquad \text{formula (64)}$$

formula (65)

$$MHal_n \qquad \text{formula (66)}$$

$$(L')_mM\underset{Hal}{\overset{Hal}{\diagup\kern-1em\diagdown}}M(L')_m \qquad \text{formula (67)}$$

where the symbols M, m, n and R have the meanings indicated above, and Hal=F, Cl, Br or I.

It is likewise possible to use metal compounds, in particular iridium compounds, which carry both alkoxide and/or halide and/or hydroxyl radicals as well as ketoketonate radicals. These compounds may also be charged. Corresponding iridium compounds which are particularly suitable as starting materials are disclosed in WO 2004/085449. Particularly suitable are [IrCl$_2$(acac)$_2$]$^-$, for example Na[IrCl$_2$(acac)$_2$], metal complexes with acetylacetonate derivatives as ligand, for example Ir(acac)$_3$ or tris(2,2,6,6-tetramethylheptane-3,5-dionato)iridium, and IrCl$_3$.xH$_2$O, where x usually stands for a number between 2 and 4.

Suitable platinum starting materials are, for example, $PtCl_2$, $K_2[PtCl_4]$, $PtCl_2(DMSO)_2$, $Pt(Me)_2(DMSO)_2$ or $PtCl_2(benzonitrile)_2$.

The synthesis of the complexes is preferably carried out as described in WO 2002/060910, WO 2004/085449 and WO 2007/065523. Heteroleptic complexes can also be synthesised, for example, in accordance with WO 2005/042548. The synthesis here can also be activated, for example, thermally, photochemically and/or by microwave radiation. In a preferred embodiment of the invention, the reaction is carried out in the melt without the use of an additional solvent. "Melt" here means that the ligand is in molten form and the metal precursor is dissolved or suspended in this melt.

These processes enable the compounds of the formula (1) according to the invention to be obtained in high purity, preferably greater than 99% (determined by means of $^1$H-NMR and/or HPLC).

The compounds according to the invention can also be rendered soluble by suitable substitution, for example by relatively long alkyl groups (about 4 to 20 C atoms), in particular branched alkyl groups, or optionally substituted aryl groups, for example, xylyl, mesityl or branched terphenyl or quaterphenyl groups. Compounds of this type are then soluble in common organic solvents, such as, for example, toluene or xylene, at room temperature in sufficient concentration to be able to process the complexes from solution. These soluble compounds are particularly suitable for processing from solution, for example by printing processes.

The present invention therefore furthermore relates to a formulation, in particular a solution, a dispersion or a miniemulsion, comprising at least one compound according to the invention and at least one solvent, in particular an organic solvent.

The complexes of the formula (1) described above or the preferred embodiments indicated above can be used as active component in the electronic device. An electronic device is taken to mean a device which comprises an anode, a cathode and at least one layer, where this layer comprises at least one organic or organometallic compound. The electronic device according to the invention thus comprises an anode, a cathode and at least one layer which comprises at least one compound of the formula (1) given above. Preferred electronic devices here are selected from the group consisting of organic electroluminescent devices (OLEDs, PLEDs), organic light-emitting transistors (O-LETs), organic light-emitting electrochemical cells (LECs), organic light-emitting electrochemical transistors (C. Yumusak, Appl. Phys. Lett. 2010, 97, 03302), organic integrated circuits (O-ICs), organic field-effect transistors (O-FETs), organic thin-film transistors (O-TFTs), organic solar cells (O—SCs), organic optical detectors, organic photoreceptors, organic field-quench devices (O-FQDs), organic plasmon emitting device (D. M. Koller et al., Nature Photonics 2008, 2, 684) or organic laser diodes (O-lasers), comprising at least one compound of the formula (1) given above in at least one layer. Particular preference is given to organic electroluminescent devices and light-emitting electrochemical cells.

Active components are generally the organic or inorganic materials which have been introduced between the anode and cathode, for example charge-injection, charge-transport or charge-blocking materials, but in particular emission materials and matrix materials. The compounds according to the invention exhibit particularly good properties as emission material in organic electroluminescent devices and in light-emitting electrochemical cells. Organic electroluminescent devices and light-emitting electrochemical cells are therefore a preferred embodiment of the invention.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers, charge-generation layers and/or organic or inorganic p/n junctions. Interlayers which have, for example, an exciton-blocking function and/or control the charge balance in the electroluminescent device may likewise be introduced between two emitting layers. However, it should be pointed out that each of these layers does not necessarily have to be present.

The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013), or systems which have more than three emitting layers. It may also be a hybrid system, where one or more layers fluoresce and one or more other layers phosphoresce.

In a preferred embodiment of the invention, the organic electroluminescent device comprises the compound of the formula (1) or the preferred embodiments indicated above as emitting compound in one or more emitting layers.

If the compound of the formula (1) is employed as emitting compound in an emitting layer, it is preferably employed in combination with one or more matrix materials. If the organic electroluminescent device is produced by vapour deposition of the materials from the gas phase, the mixture comprising the compound of the formula (1) and the matrix material comprises between 1 and 99% by vol., preferably between 2 and 90% by vol., particularly preferably between 3 and 40% by vol., especially between 5 and 15% by vol., of the compound of the formula (1), based on the mixture as a whole comprising emitter and matrix material. Correspondingly, the mixture comprises between 99.9 and 1% by vol., preferably between 99 and 10% by vol., particularly preferably between 97 and 60% by vol., in particular between 95 and 85% by vol., of the matrix material, based on the mixture as a whole comprising emitter and matrix material. If the organic electroluminescent device is produced from solution, the mixture of the compound of the formula (1) and the matrix material comprises between 0.1 and 99% by weight, preferably between 1 and 90% by weight, particularly preferably between 3 and 40% by weight, in particular between 10 and 20% by weight, of the compound of the formula (1), based on the entire mixture of emitter and matrix material. Correspondingly, the mixture comprises between 99.9 and 1% by weight, preferably between 99 and 10% by weight, particularly preferably between 97 and 60% by weight, in particular between 90 and 80% by weight, of the matrix material, based on the entire mixture of emitter and matrix material.

The matrix material employed can in general be all materials which are known for this purpose in accordance with the prior art. The triplet level of the matrix material is preferably higher than the triplet level of the emitter.

Suitable matrix materials for the compounds according to the invention are ketones, phosphine oxides, sulfoxides and sulfones, for example in accordance with WO 2004/013080, WO 2004/093207, WO 2006/005627 or WO 2010/006680, triarylamines, carbazole derivatives, for example CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example in accordance with WO 2007/063754 or WO 2008/056746, indenocarbazole derivatives, for example in accordance with WO 2010/136109 or WO 2011/000455, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, diazasilole derivatives, for example in accordance with WO 2010/054729, diazaphosphole derivatives, for example in accordance with WO 2010/054730, triazine derivatives, for example in accordance with WO 2010/015306, WO 2007/063754 or WO 2008/056746, zinc complexes, for example in accordance with EP 652273 or WO 2009/062578, dibenzofuran derivatives, for example in accordance with WO 2009/148015, or bridged carbazole derivatives, for example in accordance with US 2009/0136779, WO 2010/050778, WO 2011/042107 or WO 2011/088877.

It may also be preferred to employ a plurality of different matrix materials as a mixture, in particular at least one electron-conducting matrix material and at least one hole-conducting matrix material. A preferred combination is, for example, the use of an aromatic ketone, a triazine derivative or a phosphine oxide derivative with a triarylamine derivative or a carbazole derivative as mixed matrix for the metal complex according to the invention. Preference is likewise given to the use of a mixture of a chargetransporting matrix material and an electrically inert matrix material which is not involved or not essentially involved in charge transport, as described, for example, in WO 2010/108579.

It is furthermore preferred to employ a mixture of two or more triplet emitters together with a matrix. The triplet emitter having the shorter-wave emission spectrum serves as co-matrix for the triplet-emitter having the longer-wave emission spectrum. Thus, for example, the complexes of the formula (1) according to the invention can be employed as co-matrix for triplet emitters emitting at longer wavelength, for example for green- or redemitting triplet emitters.

The compounds according to the invention can also be employed in other functions in the electronic device, for example as hole-transport material in a hole-injection or -transport layer, as charge-generation material or as electron-blocking material. The complexes according to the invention can likewise be employed as matrix material for other phosphorescent metal complexes in an emitting layer.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag, may also be used in addition to the said metals, in which case combinations of the metals, such as, for example, Mg/Ag, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). Organic alkali-metal complexes, for example LiQ (lithium quinolinate), are likewise suitable for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order either to facilitate irradiation of the organic material (O-SCs) or the coupling-out of light (OLEDs/PLEDs, O-LASERs). Preferred anode materials here are conductive mixed metal oxides. Particular preference is given to indium tin oxide (ITO) or indium zinc oxide (IZO). Preference is furthermore given to conductive, doped organic materials, in particular conductive doped polymers, for example PEDOT, PANI or derivatives of these polymers.

All materials as are used in accordance with the prior art for the layers can generally be used in the further layers, and the person skilled in the art will be able to combine each of these materials with the materials according to the invention in an electronic device without inventive step.

The device is correspondingly structured (depending on the application), provided with contacts and finally hermetically sealed, since the lifetime of such devices is drastically shortened in the presence of water and/or air.

Preference is furthermore given to an organic electroluminescent device, characterised in that one or more layers are coated by means of a sublimation process, in which the materials are vapour-deposited in vacuum sublimation units at an initial pressure of usually less than $10^{-5}$ mbar, preferably less than $10^{-6}$ mbar. It is also possible for the initial pressure to be even lower or even higher, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing or nozzle printing, but particularly preferably LITI (light induced thermal imaging, thermal transfer printing) or ink-jet printing. Soluble compounds are necessary for this purpose, which are obtained, for example, through suitable substitution.

The organic electroluminescent device may also be produced as a hybrid system by applying one or more layers from solution and applying one or more other layers by vapour deposition. Thus, for example, it is possible to apply an emitting layer comprising a compound of the formula (1)

and a matrix material from solution and to apply a hole-blocking layer and/or an electron-transport layer on top by vacuum vapour deposition.

These processes are generally known to the person skilled in the art and can be applied by him without problems to organic electroluminescent devices comprising compounds of the formula (1) or the preferred embodiments indicated above.

Some of the main areas of application of the light-emitting devices comprising the compounds according to the invention are display or lighting technologies. It is furthermore particularly advantageous to employ the compounds and devices comprising these compounds in the area of phototherapy.

The present invention therefore furthermore relates to the use of the compounds according to the invention and devices comprising the compounds according to the invention for the treatment, prophylaxis and diagnosis of diseases. The present invention still furthermore relates to the use, of the compounds according to the invention and devices comprising the compounds according to the invention for the treatment and prophylaxis of cosmetic conditions.

The present invention furthermore relates to the compounds according to the invention for the production of devices for the therapy, prophylaxis and/or diagnosis of diseases.

Many diseases are associated with cosmetic aspects. Thus, a patient with severe acne in the facial area suffers not only from the medical causes and consequences of the disease, but also from the cosmetic accompanying circumstances.

Phototherapy or light therapy is used in many medical and/or cosmetic areas. The compounds according to the invention and the devices comprising these compounds can therefore be employed for the therapy and/or prophylaxis and/or diagnosis of all diseases and/or in all cosmetic applications for which the person skilled in the art considers the use of phototherapy. Besides irradiation, the term phototherapy also includes photodynamic therapy (PDT) and disinfection and sterilisation in general. Phototherapy or light therapy can be used for the treatment of not only humans or animals, but also any other type of living or non-living materials. These include, for example, fungi, bacteria, microbes, viruses, eukaryotes, prokaryonts, foods, drinks, water and drinking water.

The term phototherapy also includes any type of combination of light therapy and other types of therapy, such as, for example, treatment with active compounds. Many light therapies have the aim of irradiating or treating exterior parts of an object, such as the skin, wounds, mucous membranes, the eye, hair, nails, the nail bed, gums and the tongue of humans and animals. However, the treatment or irradiation according to the invention can also be carried out inside an object in order, for example, to treat internal organs (heart, lung, etc.), blood vessels or the breast.

The therapeutic and/or cosmetic areas of application according to the invention are preferably selected from the group of skin diseases and skinassociated diseases or changes or conditions, such as, for example, psoriasis, skin ageing, skin wrinkling, skin rejuvenation, enlarged skin pores, cellulite, oily/greasy skin, folliculitis, actinic keratosis, precancerous actinic keratosis, skin lesions, sun-damaged and sun-stressed skin, crows' feet, skin ulcers, acne, acne rosacea, scars caused by acne, acne bacteria, photo-modulation of greasy/oily sebaceous glands and their surrounding tissue, jaundice, jaundice of the newborn, vitiligo, skin cancer, skin tumours, Crigler-Najjar, dermatitis, atopic dermatitis, diabetic skin ulcers and desensitisation of the skin.

Particular preference is given for the purposes of the invention to the treatment and/or prophylaxis of psoriasis, acne, cellulite, skin wrinkling, skin ageing, icterus and vitiligo.

Further areas of application according to the invention for the compositions according to the invention and/or devices comprising the compositions according to the invention are selected from the group of inflammatory diseases, rheumatoid arthritis, pain therapy, treatment of wounds, neurological diseases and conditions, oedema, Paget's disease, primary and metastasising tumours, connective-tissue diseases or changes, changes in the collagen, fibroblasts and cell level originating from fibroblasts in tissues of mammals, irradiation of the retina, neovascular and hypertrophic diseases, allergic reactions, irradiation of the respiratory tract, sweating, ocular neovascular diseases, viral infections, particularly infections caused by herpes simplex or HPV (human papillomaviruses) for the treatment of warts and genital warts.

Particular preference is given for the purposes of the invention to the treatment and/or prophylaxis of rheumatoid arthritis, viral infections and pain.

Further areas of application according to the invention for the compounds according to the invention and/or devices comprising the compounds according to the invention are selected from winter depression, sleeping sickness, irradiation for improving the mood, the reduction in pain particularly muscular pain caused by, for example, tension or joint pain, elimination of joint stiffness and the whitening of the teeth (bleaching).

Further areas of application according to the invention for the compounds according to the invention and/or devices comprising the compounds according to the invention are selected from the group of disinfections. The compounds according to the invention and/or the devices according to the invention can be used for the treatment of any type of objects (non-living materials) or subjects (living materials such as, for example, humans and animals) for the purposes of disinfection, sterilisation or preservation. This includes, for example, the disinfection of wounds, the reduction in bacteria, the disinfection of surgical instruments or other articles, the disinfection or preservation of foods, liquids, in particular water, drinking water and other drinks, the disinfection of mucous membranes, gums and teeth. Disinfection here is taken to mean the reduction in the living microbiological causative agents of undesired effects, such as bacteria and germs.

For the purposes of the above-mentioned phototherapy, devices containing the compounds according to the invention preferably emit light having a wavelength between 250 and 1250 nm, particularly preferably between 300 and 1000 nm and especially preferably between 400 and 850 nm. Since many of the compounds according to the invention emit in the blue or even in the ultraviolet region and thus emit light of high energy, as is frequently necessary for phototherapy, the compounds according to the invention are particularly suitable for phototherapy.

In a particularly preferred embodiment of the present invention, the compounds according to the invention are employed in an organic light-emitting diode (OLED) or an organic light-emitting electrochemical cell (OLEC) for the purposes of phototherapy. Both the OLED and the OLEC can have a planar or fibre-like structure having any desired cross section (for example round, oval, polygonal, square)

with a single- or multilayered structure. These OLECs and/or OLEDs can be installed in other devices which comprise further mechanical, adhesive and/or electronic elements (for example battery and/or control unit for adjustment of the irradiation times, intensities and wavelengths). These devices comprising the OLECs and/or OLEDs according to the invention are preferably selected from the group comprising plasters, pads, tapes, bandages, cuffs, blankets, hoods, sleeping bags, textiles and stents.

The use of the said devices for the said therapeutic and/or cosmetic purpose is particularly advantageous compared with the prior art, since homogeneous irradiation of lower irradiation intensity is possible at virtually any site and at any time of day with the aid of the devices according to the invention using the OLEDs and/or OLECs. The irradiation can be carried out as an inpatient, as an outpatient and/or by the patient themselves, i.e. without initiation by medical or cosmetic specialists. Thus, for example, plasters can be worn under clothing, so that irradiation is also possible during working hours, in leisure time or during sleep. Complex inpatient or outpatient treatments can in many cases be avoided or their frequency reduced. The devices according to the invention may be intended for reuse or be disposable articles, which can be disposed of after use once, twice or three times.

Further advantages over the prior art are, for example, lower evolution of heat and emotional aspects. Thus, newborn being treated owing to jaundice typically have to be irradiated blindfolded in an incubator without physical contact with the parents, which represents an emotional stress situation for parents and newborn. With the aid of a blanket according to the invention comprising the OLEDs and/or OLECs according to the invention, the emotional stress can be reduced significantly. In addition, better temperature control of the child is possible due to reduced heat production of the devices according to the invention compared with conventional irradiation equipment. These above-mentioned advantages are not accompanied by an impairment of the other electronic properties.

It should be pointed out that variations of the embodiments described in the present invention fall within the scope of this invention. Each feature disclosed in the present invention can, unless explicitly excluded, be replaced by alternative features which serve the same, an equivalent or a similar purpose. Thus, each feature disclosed in the present invention should, unless stated otherwise, be regarded as an example of a generic series or as an equivalent or similar feature.

The electronic devices according to the invention, in particular organic electroluminescent devices, which comprise the compounds according to the invention are distinguished by one or more of the following surprising advantages over the prior art:

1. Organic electroluminescent devices comprising compounds of the formula (1) as emitting materials have a very good lifetime.
2. Organic electroluminescent devices comprising compounds of the formula (1) as emitting materials have excellent efficiency.
3. The metal complexes according to the invention allow access to organic electroluminescent devices which phosphoresce in the blue colour region with very good colour coordinates. In particular, blue phosphorescence with good efficiencies and lifetimes can only be achieved with great difficulty in accordance with the prior art,
4. The metal complexes according to the invention are readily accessible synthetically in high yield.

These above-mentioned advantages are not accompanied by an impairment of the other electronic properties.

The invention is explained in greater detail by the following examples without wishing to restrict it thereby. The person skilled in the art will be able to produce further electronic devices according to the invention from the descriptions without an inventive step and thus carry out the invention throughout the range claimed.

EXAMPLES

Example 1

Synthesis of the Metal Complexes

The following syntheses are carried out—unless indicated otherwise under—a protective-gas atmosphere in dried solvents. The starting materials can be purchased from ALDRICH or ABCR. The numbers in square brackets relate to the CAS numbers of the precursors and ligands that are known from the literature.

A) General Synthesis of the Dimeric µ-Chloro Precursor Complex 1 equivalent of iridium trichloride monohydrate and 2 to 2.5 equivalents of the ligand are suspended in a mixture of distilled ethoxyethanol and water in ratio 3:1 and heated under reflux overnight. The precipitate is filtered off with suction, the filtrate is evaporated, allowed to cool and filtered again. The white solid is washed with ethanol and acetone until the filtrate running off is clear.

The following compounds are obtained by this general synthesis:

| Ex. | Starting material 1 | Product | Yield |
|---|---|---|---|
| A1 | 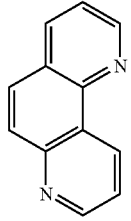 [SMILES: c1cnc2c(c1)ccc1ncccc12] [230-46-6] | 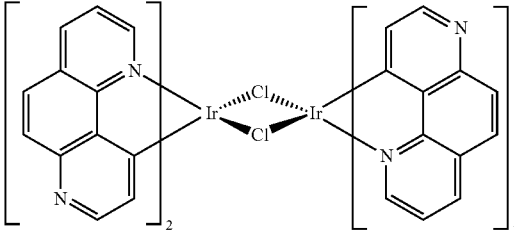 | 88% |

| Ex. | Starting material 1 | Product | Yield |
|---|---|---|---|
| A2 | [230-53-5] | | 81% |
| A3 | [230-49-9] | | 63% |
| A4 | [230-47-7] | | 44% |

B) General Synthesis of the Ir(III) Complexes 0.64 mmol of the dimeric μ-chloro precursor complex Ir$_2$(L)$_4$Cl$_2$ and 329 mg (1.28 mmol) of silver triflate are suspended in 2.7 ml of degassed ethoxyethanol, and 3.84 mmol of ligand are added. The mixture is heated at 120° C. overnight with stirring. After cooling to room temperature, the solid formed is filtered off with suction and washed with water, methanol, ether and hexane until the respective filtrate running off is clear. Purification by column chromatography on silica gel (eluent: dichloromethane) gives the complex. After sublimation in a high vacuum (p=10$^{-5}$ mbar, T=350-389° C.), the yield is 82-86% of theory with a purity of about 99.8%.

The following compounds are obtained analogously:

| Ex. | Starting material 1 | Starting material 2 | Product | Yield |
|---|---|---|---|---|
| B1 | | [230-46-6] | | 66% |

| Ex. | Starting material 1 | Starting material 2 | Product | Yield |
|---|---|---|---|---|
| B2 | [230-53-5] | | | 75% |
| B3 | [230-49-9] | | | 57% |
| B4 | [230-48-8] | | | 52% |
| B5 | | | | 51% |

The following metal complex V1 (also Ref2) is used as comparative compound. V1 is synthesised in accordance with Inorg. Chem. 2001, Vol 40, 1704.

| Ex. | |
|---|---|
| V1 (Ref2) | [337526-98-4] |

C) General Synthesis of Heteroleptic Complexes with acac: (L)$_2$Ir(acac)

A mixture of 1.0 mmol of iridium(III) chloride hydrate, 2.2 mmol of ligand, 10 ml of 2-ethoxyethanol and 0.3 ml of water is heated under reflux at 120° C. for 24 h. The reaction mixture is evaporated in vacuo, the brown residue is taken up in a mixture of 200 ml of water and 100 ml of ethanol and washed by stirring at 60° C. for 1 h. The solid is filtered off with suction and washed three times with 100 ml of ethanol each time. The brown solid is then suspended in 15 ml of ethoxyethanol, 2.0 mmol of acetylacetone and 5.0 mmol of sodium carbonate are added, and the mixture is heated under reflux for 16 h. After cooling, the precipitate is filtered off with suction, washed three times with 10 ml of a mixture of ethanol/water (1:1, v:v) each time and then three times with 10 ml of ethanol. After sublimation in a high vacuum (p=10$^{-5}$ mbar, T=350° C.-389° C.), the yield is up to 89% of theory with a purity of about 99.8%.

The following compounds are obtained analogously:

| Ex. | Starting material 1 | Starting material 2 | Product | Yield |
|---|---|---|---|---|
| C1 | | | | 57% |
| C2 | | | | 56% |
| C3 | | | | 49% |
| C4 | | | | 52% |

The following metal complex Ref3 is used as comparative compound.

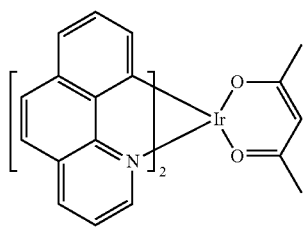

Ref3

Example 2

Quantum-Chemical Simulations of B1-B5, C1-C4, and Ref1-Ref3

The triplet and singlet level and the HOMO and LUMO positions of the organic compounds are determined via quantum-chemical calculations. To this end, the "Gaussian03W" programme package (Gaussian Inc.) is used. In order to calculate organic substances without metals, firstly a geometry optimisation is carried out using a semi-empirical "Ground State/Semi-empirical/Default Spin/ AM1" method (Charge 0/Spin Singlet). An energy calculation is subsequently carried out on the basis of the optimised geometry. The "TD-SCF/DFT/Default Spin/B3PW91"

method with the "6-31G(d)" base set is used here (Charge 0/Spin Singlet). For organometallic compounds, the geometry is optimised via the "Ground State/Hartree-Fock/Default Spin/LanL2MB" method (Charge 0/Spin Singlet). The energy calculation is carried out analogously to the organic substances as described above, with the difference that the "LanL2DZ" (pseudo=LanL2) base set is used for the metal atom and the "6-31G(d)" base set is used for the ligands. The most important results are HOMO/LUMO levels and energies for the triplet- and singlet-excited states. The first excited triplet state and the first excited singlet state are the most important. These states are known as T1 and S1. The energy calculation gives the HOMO HEh and LUMO LEh in hartree units. The HOMO and LUMO values in electron volts are determined therefrom as follows, where these relationships arise from the calibration with reference to cyclic voltammetry measurements:

HOMO(eV)=((*HEh*\*27.212)−0.9899)/1.1206

LUMO(eV)=((*LEh*\*27.212)−2.0041)/1.385

For the purposes of this application, these values are to be regarded as the energetic position of the HOMO level or LUMO level of the materials. As an example, an HOMO of −0.20972 hartrees and an LUMO of −0.06756 hartrees are obtained for compound B1 (see also Table 1) from the calculation, which corresponds to a calibrated HOMO of −5.98 eV and a calibrated LUMO of −2.77 eV.

The simulated energy levels of metal complexes B1-B5 and C1-C4 according to the invention are summarised in Table 1 compared with Ref2 and Ref3, where the values for the pale-blue emitter Ref1 which is known from the literature are also indicated as an additional reference. Compared with Ref1, all B1-B5 give greater or at least comparable T1 levels. These compounds are therefore suitable as blue or even as deep-blue triplet emitters. In particular, B3 even has a T1 level of greater than 2.9 eV. All B1-B5 have a T1 level of at least 0.14 eV higher than Ref2.

C1-C4 also have a T1 level which is significantly higher than that of Ref3.

TABLE 1

Summary of the energy levels of B1 to B5, C1 to C4 and Ref1-Ref3

| Compound | Homo corr. [eV] | Lumo corr. [eV] | Singlet S1 [eV] | Triplet T1 [eV] |
| --- | --- | --- | --- | --- |
| Ref1 | −5.90 | −2.80 | 2.97 | 2.78 |
| B1 | −5.98 | −2.77 | 3.02 | 2.78 |
| B2 | −6.32 | −3.17 | 2.89 | 2.77 |
| B3 | −6.37 | −3.05 | 3.11 | 2.91 |
| B4 | −6.39 | −3.11 | 3.03 | 2.81 |
| B5 | −6.09 | −3.02 | 2.86 | 2.75 |
| Ref2 | −5.33 | −2.51 | 2.69 | 2.61 |
| Ref3 | −5.23 | −2.57 | 2.64 | 2.44 |
| C1 | −5.78 | −2.76 | 2.84 | 2.72 |
| C2 | −6.03 | −3.10 | 2.70 | 2.63 |

TABLE 1-continued

Summary of the energy levels of B1 to B5, C1 to C4 and Ref1-Ref3

| Compound | Homo corr. [eV] | Lumo corr. [eV] | Singlet S1 [eV] | Triplet T1 [eV] |
| --- | --- | --- | --- | --- |
| C3 | −6.07 | −2.98 | 2.88 | 2.79 |
| C4 | −6.08 | −3.06 | 2.78 | 2.67 |

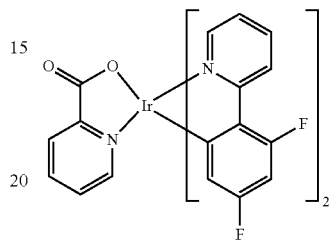

Ref1

In order to see the advantages of metal complexes according to the invention even more clearly, further compounds were also simulated.

FIG. 1 shows the T1 and S1 level of various metal complexes, where the bridge —Y— is equal to —HC═CH— and the carbon atoms in the ligand have been replaced by 0, 1 or 2 N atoms. Bx corresponds to a metal complex according to the invention and Vx corresponds to the comparable metal complex in accordance with the prior art. It is clear that the metal complexes according to the invention have a significantly higher T1 level than the comparable metal complexes, such as, for example, B1 compared with V1 to V7, B2, B3 and B4 compared with V8 to V10 and B6 compared with V10.

Figure 2:
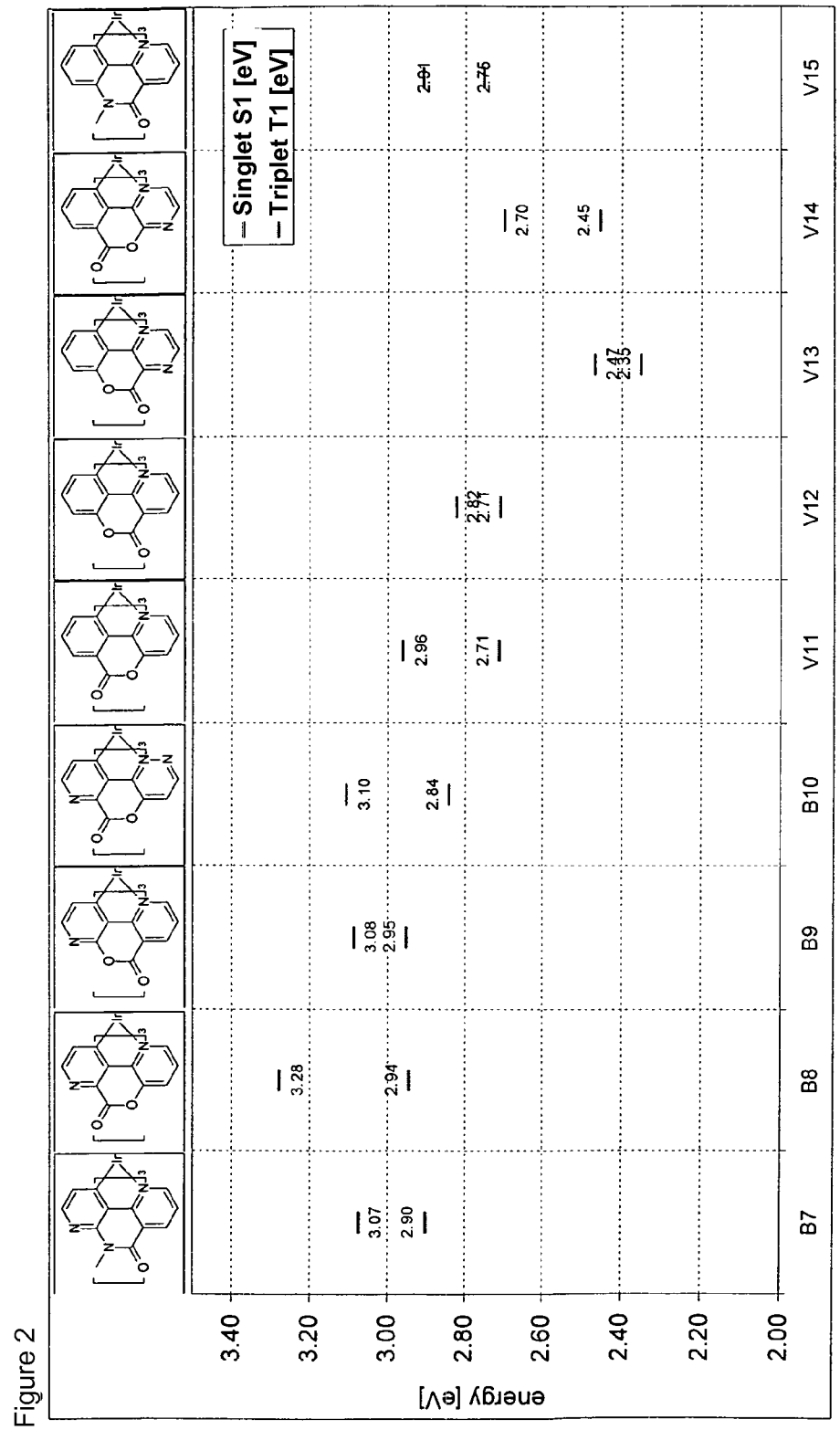
FIG. 2 shows the T1 and S1 level of various metal complexes, where the bridge —Y— contains a keto group and the carbon atoms in the ligand have been replaced by 0 or 1N atoms.

FIG. 2 shows the T1 and S1 level of various metal complexes, where the bridge —Y— contains a keto group and the carbon atoms in the ligand have been replaced by 0 or 1 N atoms. It is clear that the metal complexes according to the invention have a significantly higher T1 level than the comparable metal complexes, such as, for example, B7 compared with V15, B8 compared with V11 and V14 and B9 compared with V12 and V13. Furthermore, metal complex B10 according to the invention also exhibits a highly promising T1 level.

Figure 3:
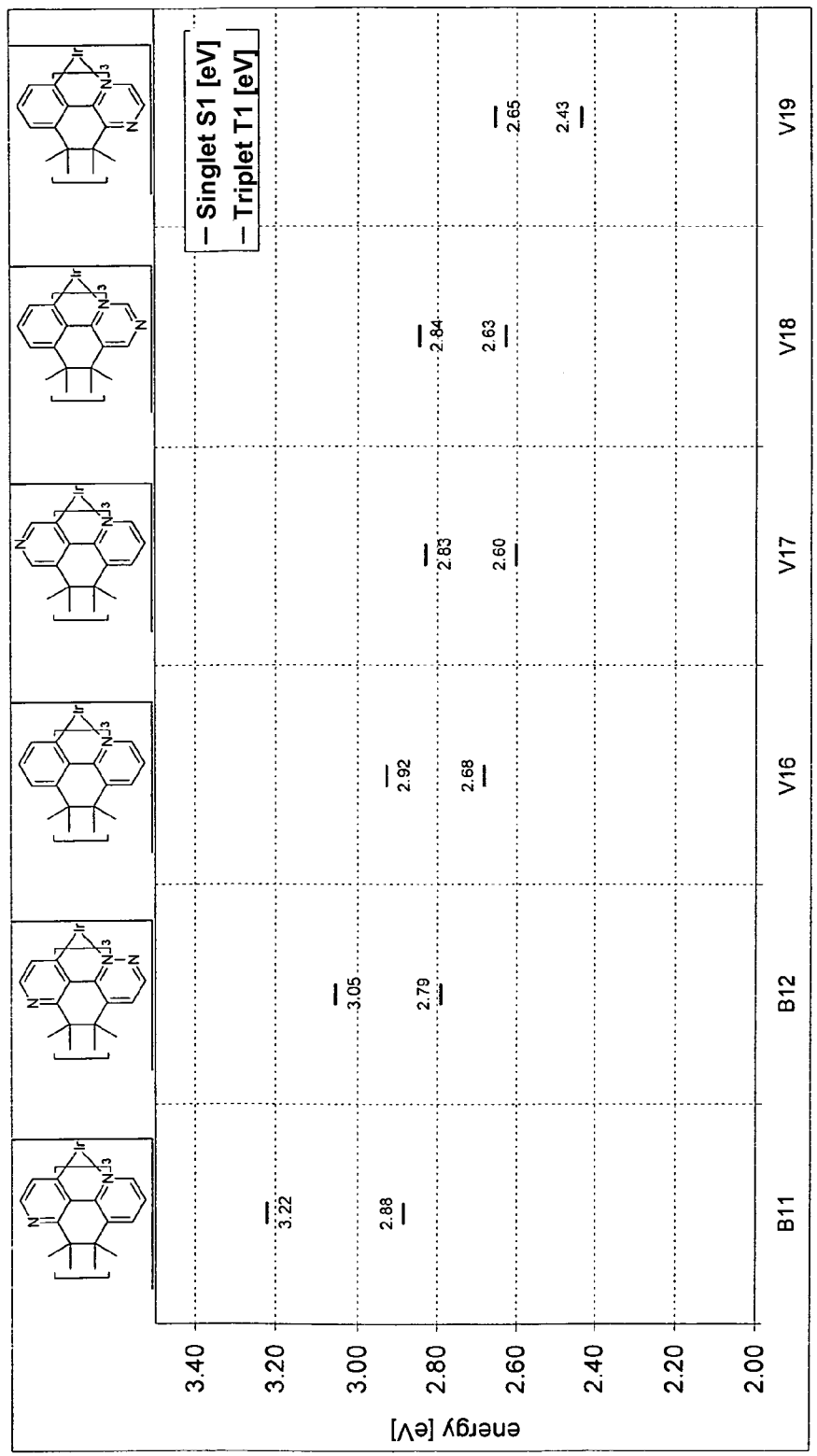
FIG. 3 shows the T1 and S1 level of various metal complexes, where the bridge —Y— is equal to —C(CH$_3$)$_2$—C(CH$_3$)$_2$— and the carbon atoms in the ligand have been replaced by 0 or 1 N atom.

FIG. 3 shows the T1 and S1 level of various metal complexes, where the bridge —Y— is equal to —C(CH₃)₂—C(CH₃)₂— and the carbon atoms in the ligand have been replaced by 0 or 1 N atom. It is clear that the metal complexes according to the invention have a significantly higher T1 level than the comparable metal complexes, such as, for example, B11 compared with V16 to V19. Furthermore, metal complex B12 according to the invention exhibits a highly promising T1 level.

Example 3

Photoluminescence Investigations

The photoluminescence spectra of metal complexes B1-B4 according to the invention and of comparative compound V1 are measured in a solution of toluene in a concentration of about 0.1 mol %. The excitation wavelength is always the maximum of the absorption. The CIE coordinates, which are summarised in Table 2, are calculated from the photoluminescence spectrum. Compound B3 exhibits blue emission with the lowest colour coordinates (CIE y=0.22), followed by B4 with CIE y=0.27.

TABLE 2

|    | CIEx | CIEy |
|----|------|------|
| B1 | 0.15 | 0.32 |
| B2 | 0.16 | 0.30 |
| B3 | 0.16 | 0.22 |
| B4 | 0.17 | 0.27 |
| V1 | 0.44 | 0.54 |

Example 4

Solutions and Compositions Comprising B1, V1 and Matrix Materials

For use in organic electronic devices, formulations, in particular solutions, comprising the compounds according to the invention are prepared. For this purpose, B1 is used as blue emitter for an organic electroluminescent device. In order to construct a phosphorescent electroluminescent device, one or more matrix materials are additionally used. The matrix material should occupy a T1 level higher than that of the emitter.

The following triplet matrix materials TMM1 and TMM2 are used as co-matrix materials. TMM1 is synthesised in accordance with WO 2005/003253 A2 and TMM2 is synthesised in accordance with WO 2009/124627.

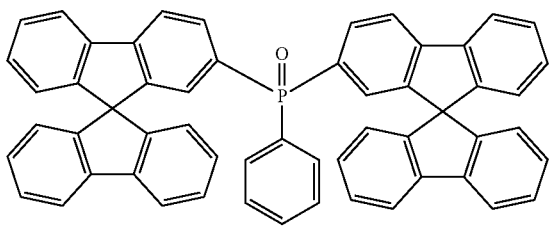

TMM1

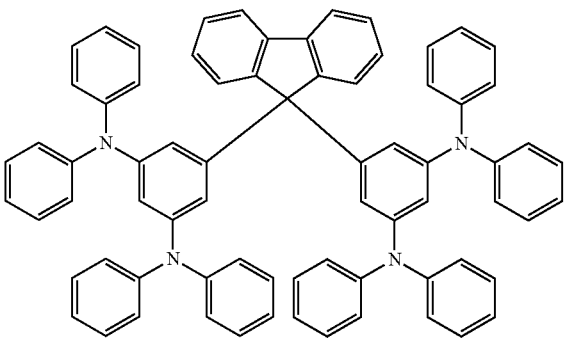

TMM2

The energy levels of the components in the mixtures are summarised in Table 3.

TABLE 3

Summary of the energy levels of B1, V1, TMM1 and TMM2.

|      | Homo corr. [eV] | Lumo corr. [eV] | Singlet S1 [eV] | Triplet T1 [eV] |
|------|-----------------|-----------------|-----------------|-----------------|
| B1   | −5.98           | −2.77           | 3.02            | 2.78            |
| V1   | −5.33           | −2.51           | 2.69            | 2.61            |
| TMM1 | −5.99           | −2.47           | 3.80            | 2.86            |
| TMM2 | −5.23           | −2.13           | 3.04            | 2.82            |

Solutions are prepared as follows: firstly, 150 mg of the mixture according to Table 4 are dissolved in 10 ml of chlorobenzene and stirred until the solution is clear. The solution is filtered using a Millipore Millex LS, Hydrophobic PTFE 5.0 µm filter. Solution 2 is used as comparison. Polystyrene (PS) (from Fluka with Mw 200,000 kg/mol) is mixed in in order to obtain better layer formation.

TABLE 4

Composition of the solutions

|                        | Composition              | Ratio (based on weight) | Solvent       | Concentration |
|------------------------|--------------------------|-------------------------|---------------|---------------|
| Solution 1 (for OLED1) | TMM1 + TMM2 + B1 + PS    | 40%:15%:15%:30%         | Chlorobenzene | 15 mg/ml      |
| Solution 2 (for OLED2) | TMM1 + TMM2 + V1 + PS    | 40%:15%:15%:30%         | Chlorobenzene | 15 mg/ml      |

Solutions 1 and 2 are used in order to coat the emitting layer of OLEDs. The corresponding solid composition can be obtained by evaporating the solvent from the solutions. This can be used for the preparation of further formulations.

Example 5

Production of OLEDs from Solutions

OLED1 and OLED2 having a structure in accordance with the prior art ITO/PEDOT/interlayer/EML/cathode are produced in accordance with the following procedure using the corresponding solutions, as summarised in Table 4:

1) Coating of 80 nm of PEDOT (Baytron P AI 4083) onto an ITO-coated glass substrate by spin coating in a clean room and then drying of the PEDOT layer by heating at 180° C. for 10 min.
2) Coating of a 20 nm interlayer by spin coating of a toluene solution of HIL-012 (Merck KGaA) in a concentration of 0.5% by weight in a glovebox.
3) Drying of interlayer HIL-012 by heating at 180° C. for 1 h in a glovebox.
4) Coating of an 80 nm emitting layer by spin coating of a solution according to Table 4.
5) Drying of the device by heating at 120° C. for 30 min.
6) Application of a Ba/Al cathode by vapour deposition (3 nm+150 nm).
7) Encapsulation of the device.

Example 6

Measurements and Comparison of the Results of OLED1 and OLED2

The OLEDs obtained in this way are characterised by standard methods. The following properties are measured here: UIL characteristics, electroluminescence spectrum, colour coordinates, efficiency, operating voltage and lifetime. The results are summarised in Table 5, where OLED2 serves as comparison in accordance with the prior art. In Table 5, EQE stands for the external quantum efficiency, U(100) stands for the voltage at 100 cd/m$^2$ and U(1000) stands for the voltage at 1000 cd/m$^2$.

TABLE 5

Measurement results with OLED1 and OLED2

| | Max. eff. [cd/A] | U(100) [V] | U(1000) [V] | CIE @ 100 cd/m$^2$ | EQE [%] |
|---|---|---|---|---|---|
| OLED1 | 5.2 | 7.4 | 9.1 | 0.16/0.37 | 2.25 |
| OLED2 (cmp.) | 5.3 | 9.2 | 11 | 0.45/0.56 | 1.82 |

As can be seen from Table 5, an improved phosphorescent OLED with respect to colour and efficiency, in particular to the colour, is obtained using emitter B1 according to the invention.

Example 7

Production of OLEDs by Vapour Deposition

The production of OLEDs according to the invention and OLEDs in accordance with the prior art by vapour deposition is carried out by a general process in accordance with WO 2004/058911, which is adapted to the circumstances described here (layer-thickness variation, materials used).

The results for various OLEDs are presented in the following examples (see Tables 6 and 7). Glass plates coated with structured ITO (indium tin oxide) in a thickness of 50 nm are coated with 80 nm of PEDOT (poly(3,4-ethylene-dioxy-2,5-thiophene), applied by spin coating from water; purchased from H. C. Starck, Goslar, Germany) for improved processing. These coated glass plates form the substrates to which the OLEDs are applied. The OLEDs have in principle the following layer structure: substrate/optional hole-injection layer (HIL1)/optional hole-injection layer (HIL2)/hole-transport layer (HTL)/electron-blocking layer (EBL)/emission layer (EML)/optional hole-blocking layer (HBL)/electron-transport layer (ETL) and finally a cathode. The cathode is formed by an aluminium layer with a thickness of 100 nm.

Firstly, vacuum-processed OLEDs are described. For this purpose, all materials are applied by thermal vapour deposition in a vacuum chamber. The emission layer here always consists of at least one matrix material (host material) and an emitting dopant (emitter), which is admixed with the matrix material or matrix materials in a certain proportion by volume by coevaporation. An expression such as TMM1:TMM2:B1 (80%:10%:10%) here means that material TMM1 is present in the layer in a proportion by volume of 80%, TMM2 is present in the layer in a proportion of 10% and B1 is present in the layer in a proportion of 10%. Analogously, the electron-transport layer may also consist of a mixture of two materials. The precise structure of the OLEDs is shown in Table 6. Apart from TMM1 and TMM2, the materials used for the production of the OLEDs are shown in Table 8.

The OLEDs are characterised by standard methods. For this purpose, the electroluminescence spectra, the current efficiency (measured in cd/A), the EQE and the voltage (measured at 1000 cd/m$^2$ in V) are determined from current/voltage/luminance characteristic lines (IUL characteristic lines).

The compounds according to the invention can be employed, inter alia, as phosphorescent emitter materials in the emission layer in OLEDs. As comparison in accordance with the prior art, compounds Ref2 and Ref3 are used. The results for the OLEDs are summarised in Table 7.

TABLE 6

Structure of the OLEDs

| Ex. | HIL1 Thickness | HIL2 Thickness | EBL Thickness | EML Thickness | HBL Thickness | ETL Thickness |
|---|---|---|---|---|---|---|
| Ref2 | HTM1 20 nm | EBM1 5 m | EBM2 15 nm | TMM1:TMM2:Ref2 (70%:20%:10%) 40 nm | HBM1 10 nm | ETM1:LiQ (50%:50%) 30 nm |
| Ref3 | HTM1 20 nm | EBM1 5 m | EBM2 15 nm | TMM1:TMM2:Ref3 (70%:20%:10%) 40 nm | HBM1 10 nm | ETM1:LiQ (50%:50%) 30 nm |

TABLE 6-continued

Structure of the OLEDs

| Ex. | HIL1 Thickness | HIL2 Thickness | EBL Thickness | EML Thickness | HBL Thickness | ETL Thickness |
|---|---|---|---|---|---|---|
| B1 | HTM1 20 nm | EBM1 5 m | EBM2 15 nm | TMM1:TMM2:B1 (70%:20%:10%) 40 nm | HBM1 10 nm | ETM1:LiQ (50%:50%) 30 nm |
| B2 | HTM1 20 nm | EBM1 5 m | EBM2 15 nm | TMM1:TMM2:B2 (70%:20%:10%) 40 nm | HBM1 10 nm | ETM1:LiQ (50%:50%) 30 nm |
| B3 | HTM1 20 nm | EBM1 5 m | EBM2 15 nm | TMM1:TMM2:B3 (70%:20%:10%) 40 nm | HBM1 10 nm | ETM1:LiQ (50%:50%) 30 nm |
| B4 | HTM1 20 nm | EBM1 5 m | EBM2 15 nm | TMM1:TMM2:B4 (70%:20%:10%) 40 nm | HBM1 10 nm | ETM1:LiQ (50%:50%) 30 nm |
| B5 | HTM1 20 nm | EBM1 5 m | EBM2 15 nm | TMM1:TMM2:B5 (70%:20%:10%) 40 nm | HBM1 10 nm | ETM1:LiQ (50%:50%) 30 nm |
| C1 | HTM1 20 nm | EBM1 5 m | EBM2 15 nm | TMM1:TMM2:C1 (70%:20%:10%) 40 nm | HBM1 10 nm | ETM1:LiQ (50%:50%) 30 nm |
| C2 | HTM1 20 nm | EBM1 5 m | EBM2 15 nm | TMM1:TMM2:C2 (70%:20%:10%) 40 nm | HBM1 10 nm | ETM1:LiQ (50%:50%) 30 nm |
| C3 | HTM1 20 nm | EBM1 5 m | EBM2 15 nm | TMM1:TMM2:C3 (70%:20%:10%) 40 nm | HBM1 10 nm | ETM1:LiQ (50%:50%) 30 nm |
| C4 | HTM1 20 nm | EBM1 5 m | EBM2 15 nm | TMM1:TMM2:C4 (70%:20%:10%) 40 nm | HBM1 10 nm | ETM1:LiQ (50%:50%) 30 nm |

TABLE 7

Use of compounds according to the invention as phosphorescent emitter materials in phosphorescent OLEDs

| Ex. | Voltage (V) 1000 cd/m$^2$ | Efficiency (cd/A) at 1000 cd/m$^2$ | CIE x/y at 1000 cd/m$^2$ | EQE at 1000 cd/m$^2$ |
|---|---|---|---|---|
| Ref2 | 6.0 | 22.0 | 0.34/0.62 | 9.3% |
| Ref3 | 6.1 | 23.0 | 0.38/0.59 | 6.5% |
| B1 | 7.7 | 6.7 | 0.15/0.20 | 4.8% |
| B2 | 6.6 | 14.7 | 0.15/0.27 | 8.1% |
| B3 | 8.1 | 5.9 | 0.15/0.19 | 4.3% |
| B4 | 7.9 | 8.2 | 0.16/0.21 | 5.8% |
| B5 | 6.5 | 18.0 | 0.15/0.30 | 9.6% |
| C1 | 4.3 | 36.3 | 0.36/0.61 | 9.7% |
| C2 | 5.7 | 34.0 | 0.34/0.62 | 9.3% |
| C3 | 6.1 | 10.5 | 0.16/0.27 | 5.7% |
| C4 | 5.7 | 32.0 | 0.32/0.63 | 8.9% |

TABLE 8

Structural formulae of the materials used

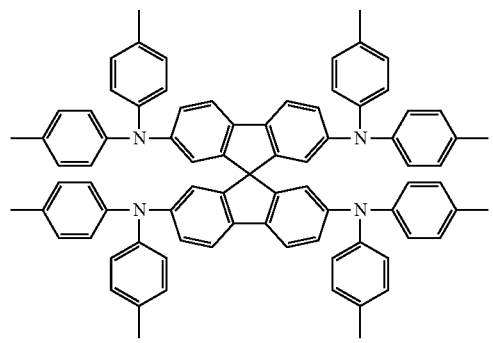

HTM1

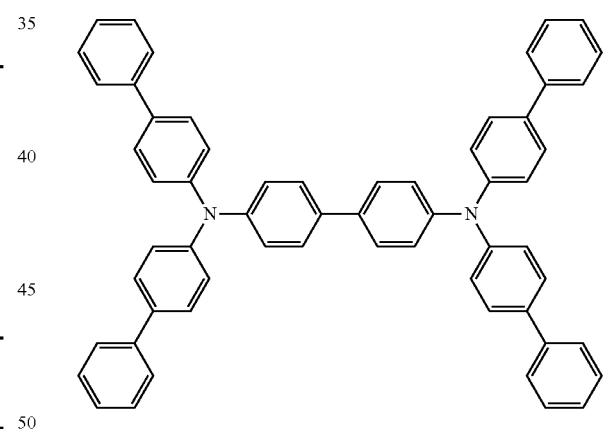

EBM1

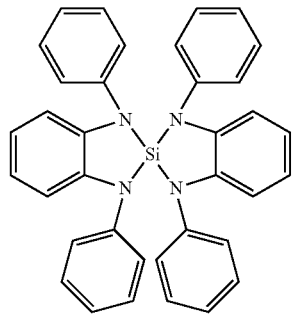 [SMILES: c1ccc(N2c3ccccc3N(c3ccccc3)[Si]23N(c2ccccc2)c2ccccc2N3c2ccccc2)cc1]

EBM2

TABLE 8-continued

Structural formulae of the materials used

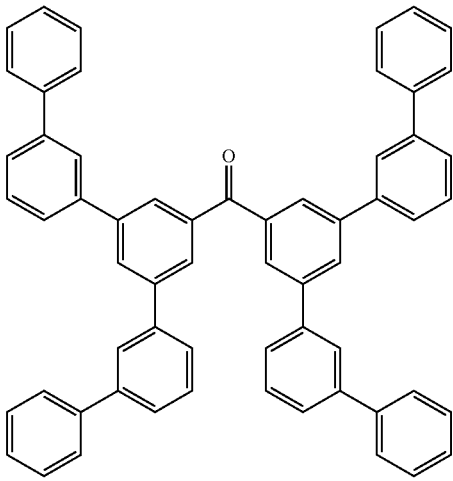 [SMILES: O=C(c1cc(-c2cccc(-c3ccccc3)c2)cc(-c2cccc(-c3ccccc3)c2)c1)c1cc(-c2cccc(-c3ccccc3)c2)cc(-c2cccc(-c3ccccc3)c2)c1]

HBM1

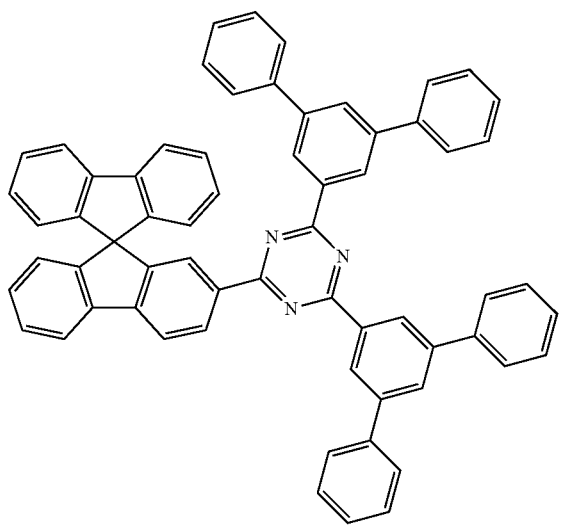 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]

ETM1

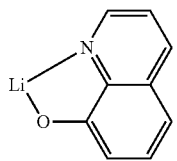

LiQ

Further optimisations can be achieved by means of various possibilities on the basis of the present technical teaching according to the invention without being inventive in the process. Thus, a further optimisation can be achieved, for example, by the use of another matrix or mixed matrices in the same or another concentration or by other interlayer materials.

The invention claimed is:

1. A compound of the formula (1),

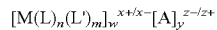

formula (1)

where the compound of the general formula (1) contains a moiety $M(L)_n$ of the formula (2):

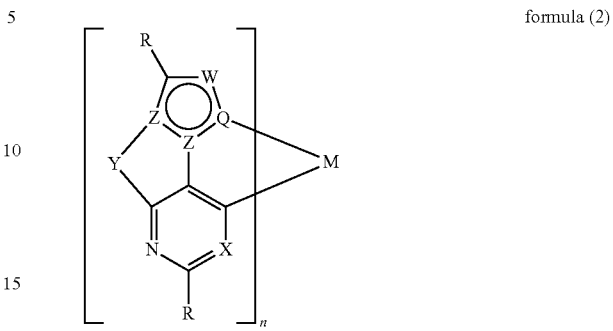

formula (2)

where the following applies to the symbols and indices used:

M is a transition metal;

Q is on each occurrence, identically or differently, N;

X is on each occurrence, identically or differently, CR or N;

Y is on each occurrence, identically or differently, a substituted or unsubstituted diatomic bridge containing, as bridge atoms, two atoms selected, identically or differently on each occurrence, from the group consisting of C, N, O, S, Si or P;

W is on each occurrence, identically or differently, CR=CR or CR=N;

Z is C;

R is on each occurrence, identically or differently, H, D, F, Cl, Br, I, $N(R^1)_2$, CN, $NO_2$, OH, COOH, C(=O)N $(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^1$, where one or more non-adjacent $CH_2$ groups is optionally replaced by $R^1C=CR^1$, C=C, $Si(R^1)_2$, C=O, $NR^1$, O, S or $CONR^1$ and where one or more H atoms is optionally replaced by D, F, Cl, Br, I or CN, or an aromatic or heteroaromatic ring system having 5 to 60 aromatic ring atoms, which optionally in each case be substituted by one or more radicals $R^1$, or an aryloxy or heteroaryloxy group having 5 to 40 aromatic ring atoms, which is optionally substituted by one or more radicals $R^1$, or an aralkyl or heteroaralkyl group having 5 to 40 aromatic ring atoms, which is optionally substituted by one or more radicals $R^1$, or a diarylamino group, diheteroarylamino group or arylheteroarylamino group having 10 to 40 aromatic ring atoms, which is optionally substituted by one or more radicals $R^1$; two adjacent radicals R here may also form a mono- or polycyclic, aliphatic, aromatic or heteroaromatic ring system with one another;

$R^1$ is on each occurrence, identically or differently, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals R², where one or more non-adjacent CH₂ groups is optionally replaced by R²C=CR², C≡C, Si(R²)₂, C=O, NR², O, S or CONR² and where one or more H atoms is optionally replaced by D, F, Cl, Br, I, CN or NO₂, or an aromatic or heteroaromatic ring system having 5 to 60 aromatic ring atoms, which may in each case be substituted by one or more radicals R², or an aryloxy or heteroaryloxy group having 5 to 40 aromatic ring atoms, which is optionally substituted by one or more radicals R², or an aralkyl or heteroaralkyl group having 5 to 40 aromatic ring atoms, which is optionally substituted by one or more radicals R², or a diarylamino group, diheteroarylamino group or arylheteroarylamino group having 10 to 40 aromatic ring atoms, which is optionally substituted by one or more radicals R²; two or more adjacent radicals R² here may form a mono- or polycyclic, aliphatic ring system with one another;

R² is on each occurrence, identically or differently, H, D, F or an aliphatic, aromatic and/or heteroaromatic hydrocarbon radical having 1 to 20 C atoms, in which, in addition, one or more H atoms is optionally replaced by F; two or more substituents R² here may also form a mono- or polycyclic, aliphatic ring system with one another;

L' is, identically or differently on each occurrence, any desired co-ligand;

A is a counterion;

n is 1, 2 or 3;

m is 0, 1, 2, 3 or 4;

w is 1, 2 or 3;

x, y, z are on each occurrence, identically or differently, 0, 1, 2 or 3; where (w·x)=(y·z);

a plurality of ligands L here may also be linked to one another or L is optionally linked to L' via any desired bridge V and thus form a tridentate, tetradentate, pentadentate or hexadentate ligand system;

furthermore, a substituent R may also additionally be coordinated to the metal.

2. The compound according to claim 1, wherein M is selected from the group consisting of chromium, molybdenum, tungsten, rhenium, ruthenium, osmium, rhodium, iridium, nickel, palladium, platinum, copper, silver and gold.

3. The compound according to claim 1, wherein one of the two bridge atoms in the group Y represents a carbon atom and in that the other bridge atom is selected from C, N or O, where the atoms may in each case be substituted by radicals R.

4. The compound according to claim 1, wherein the bridge Y is selected from the structures —CR=CR—, —CR=N—, —C(=O)—CR₂—, —C(=O)—NR—, —C(=O)—O— or —CR₂—CR₂— or from the structures of the formulae (A) to (E),

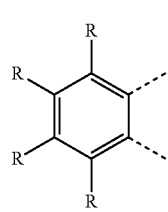

formula (A)

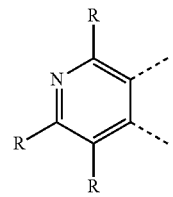

formula (B)

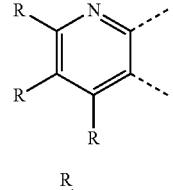

forumula (C)

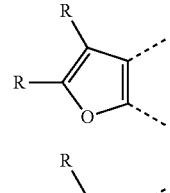

formula (D)

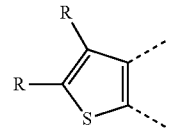

formula (E)

where R has the meaning given in claim 1 and the dashed bonds in each case indicate the bonding of this group in the corresponding ligand.

5. The compound according to claim 1, wherein X stands for CR or CH.

6. A compound of the formula (1), $$[M(L)_n(L')_m]_w^{x+/x-}[A]_y^{z-/z+}$$ formula (1)

where the compound of the general formula (1) contains a moiety $M(L)_n$ of the formula (2):

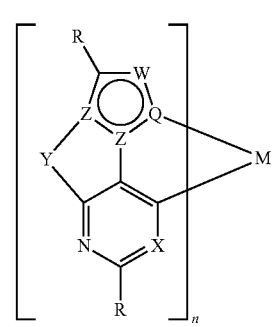

formula (2)

where the following applies to the symbols and indices used:

M is a transition metal;

Q is on each occurrence, identically or differently, N;

X is on each occurrence, identically or differently, CR or N;

Y is on each occurrence, identically or differently, a substituted or unsubstituted diatomic bridge containing, as bridge atoms, two atoms selected, identically or differently on each occurrence, from the group consisting of C, N, O, S, Si or P;

W is on each occurrence, identically or differently, CR, N, CR=CR or CR=N if Q stands for N, with the proviso that W stands for CR=CR or CR=N if Y stands for CR=CR or for CR=N;
or W is NR if Q stands for C;

Z is C if W in this ligand stands for CR=CR or CR=N; or one Z stands for C and the other Z stands for N if W in this ligand stands for CR or N or NR;

R is on each occurrence, identically or differently, H, D, F, Cl, Br, I, $N(R^1)_2$, CN, $NO_2$, OH, COOH, C(=O)N$(R^1)_2$, $Si(R^1)_3$, $B(OR^1)_2$, $C(=O)R^1P(=O)(R^1)_2$, $S(=O)R^1$, $S(=O)_2R^1$, $OSO_2R^1$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^1$, where one or more non-adjacent $CH_2$ groups is optionally replaced by $R^1C=CR^1$, C≡C, $Si(R^1)_2$, C=O, $NR^1$, O, S or $CONR^1$ and where one or more H atoms is optionally replaced by D, F, Cl, Br, I or CN, or an aromatic or heteroaromatic ring system having 5 to 60 aromatic ring atoms, which optionally in each case be substituted by one or more radicals $R^1$, or an aryloxy or heteroaryloxy group having 5 to 40 aromatic ring atoms, which is optionally substituted by one or more radicals $R^1$, or an aralkyl or heteroaralkyl group having 5 to 40 aromatic ring atoms, which is optionally substituted by one or more radicals $R^1$, or a diarylamino group, diheteroarylamino group or arylheteroarylamino group having 10 to 40 aromatic ring atoms, which is optionally substituted by one or more radicals $R^1$; two adjacent radicals R here may also form a mono- or polycyclic, aliphatic, aromatic or heteroaromatic ring system with one another;

$R^1$ is on each occurrence identically or differently, H D F Cl Br, I, $N(R^2)_2$, CN, $NO_2Si(R^2)_3$, $B(OR^2)_2$, $C(=O)R^2$, $P(=O)(R^2)_2$, $S(=O)R^2$, $S(=O)R^2$, $OSO_2R^2$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^2$, where one or more non-adjacent $CH_2$ groups is optionally replaced by $R^2C=CR^2$, C≡C, $Si(R^2)_2$, C=O, $NR^2$, O, S or $CONR^2$ and where one or more H atoms is optionally replaced by D, F, Cl, Br, I, CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which is optionally substituted by one or more radicals $R^2$, or an aralkyl or heteroaralkyl group having 5 to 40 aromatic ring atoms, which is optionally substituted by one or more radicals $R^2$, or a diarylamino group, diheteroarylamino group or arylheteroarylamino group having 10 to 40 aromatic ring atoms, which is optionally substituted by one or more radicals $R^2$; two or more adjacent radicals $R^2$ here may form a mono- or polycyclic, aliphatic ring system with one another;

$R^2$ is on each occurrence, identically or differently, H, D, F or an aliphatic, aromatic and/or heteroaromatic hydrocarbon radical having 1 to 20 C atoms, in which, in addition, one or more H atoms is optionally replaced by F; two or more substituents $R^2$ here may also form a mono- or polycyclic, aliphatic ring system with one another;

L' is, identically or differently on each occurrence, any desired co-ligand;

A is a counterion;

n is 1, 2 or 3;

m is 0, 1, 2, 3 or 4;

w is 1, 2 or 3;

x, y, z are on each occurrence, identically or differently, 0, 1, 2 or 3; where (w ·x)=(y ·z);

a plurality of ligands L here may also be linked to one another or L is optionally linked to L' via any desired bridge V and thus form a tridentate, tetradentate, pentadentate or hexadentate ligand system;

furthermore, a substituent R may also additionally be coordinated to the metal, wherein the substituent R in the ortho-position to the metal coordination represents a group which is likewise coordinated to the metal M.

7. A compound selected from the compounds of the following formulae (17) to (22),

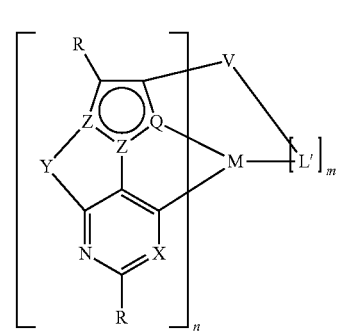

formula (17)

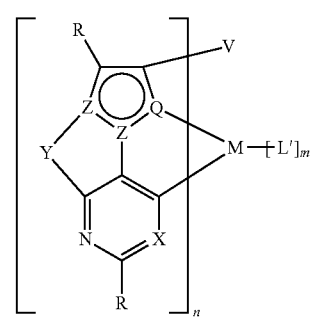

formula (18)

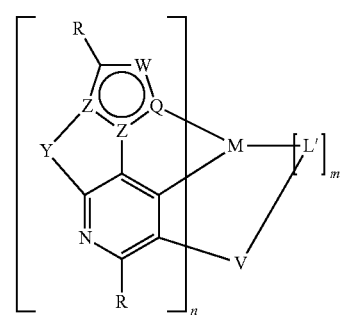

formula (19)

-continued

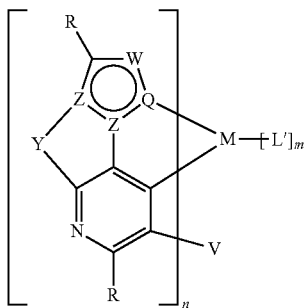

formula (20)

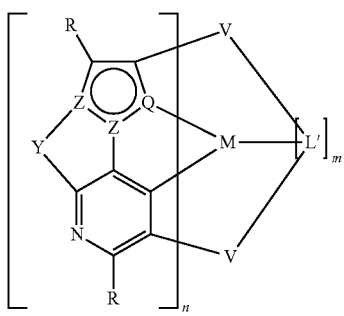

formula (21)

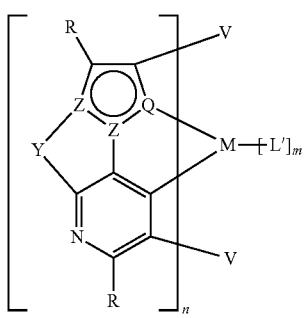

formula (22)

M is a transition metal;
Q is on each occurrence, identically or differently, N;
X is on each occurrence, identically or differently, CR or N;
Y is on each occurrence, identically or differently, a substituted or unsubstituted diatomic bridge containing, as bridge atoms, two atoms selected, identically or differently on each occurrence, from the group consisting of C, N, O, S, Si or P;
W is on each occurrence, identically or differently, CR, N, CR=CR or CR=N if Q stands for N, with the proviso that W stands for CR=CR or CR=N if Y stands for CR=CR or for CR=N;
or W is NR if Q stands for C;
Z is C if W in this ligand stands for CR=CR or CR=N; or one Z stands for C and the other Z stands for N if W in this ligand stands for CR or N or NR;
R is on each occurrence, identically or differently, H, D, F, Cl, Br, I, $N(R^1)_2$, CN, $NO_2$, OH, COON, $C(=O)N(R^1)_2$, $Si(R^1)_3$, $B(OR^1)_2$, $C(=O)R^1$, $P(=O)(R^1)_2$, $S(=O)R^1$, $S(=O)_2R^1$, $OSO_2R^1$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^1$, where one or more non-adjacent $CH_2$ groups is optionally replaced by $R^1C=CR^1$, C≡C, $Si(R^1)_2$, C=O, $NR^1$, O, S or $CONR^1$ and where one or more H atoms is optionally replaced by D, F, Cl, Br, I or CN, or an aromatic or heteroaromatic ring system having 5 to 60 aromatic ring atoms, which optionally in each case be substituted by one or more radicals R', or an aryloxy or heteroaryloxy group having 5 to 40 aromatic ring atoms, which is optionally substituted by one or more radicals R', or an aralkyl or heteroaralkyl group having 5 to 40 aromatic ring atoms, which is optionally substituted by one or more radicals R', or a diarylamino group, diheteroarylamino group or arylheteroarylamino group having 10 to 40 aromatic ring atoms, which is optionally substituted by one or more radicals $R^1$; two adjacent radicals R here may also form a mono- or polycyclic, aliphatic, aromatic or heteroaromatic ring system with one another;
R' is on each occurrence, identically or differently, H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^2$, where one or more non-adjacent $CH_2$ groups is optionally replaced by $R^2C=CR^2$, C≡C, $Si(R^2)_2$, C=O, $NR^2$, O, S or $CONR^2$ and where one or more H atoms is o tionall replaced by D F Cl Br I CN or $NO_2$, or an aromatic or heteroaromatic ring system having 5 to 60 aromatic ring atoms, which may in each case be substituted by one or more radicals $R^2$, or an aryloxy or heteroaryloxy group having 5 to 40 aromatic ring atoms, which is optionally substituted by one or more radicals $R^2$, or an aralkyl or heteroaralkyl group having 5 to 40 aromatic ring atoms, which is optionally substituted by one or more radicals $R^2$, or a diarylamino group, diheteroarylamino group or arylheteroarylamino group having 10 to 40 aromatic ring atoms, which is optionally substituted by one or more radicals $R^2$; two or more adjacent radicals $R^2$ here may form a mono- or polycyclic, aliphatic ring system with one another;
$R^2$ is on each occurrence, identically or differently, H, D, F or an aliphatic, aromatic and/or heteroaromatic hydrocarbon radical having 1 to 20 C atoms, in which, in addition, one or more H atoms is optionally replaced by F; two or more substituents $R^2$ here may also form a mono- or polycyclic, aliphatic ring system with one another;
is, identically or differently on each occurrence, any desired co-ligand;
n is 1, 2 or 3;
m is 0, 1, 2, 3 or 4;
a plurality of ligands L here may also be linked to one another or L is optionally linked to L' via any desired bridge V and thus form a tridentate, tetradentate, pentadentate or hexadentate ligand system;
furthermore, a substituent R may also additionally be coordinated to the metal;
V represents a bridging unit containing 1 to 80 atoms from the third, fourth, fifth and/or sixth main group or a 3- to 6-membered homo- or heterocycle which covalently bonds the part-ligands L to one another or L to L'.

8. The compound according to claim 1, wherein L' is selected, identically or differently on each occurrence, from the group consisting of carbon monoxide, nitrogen monoxide, alkylcyanides, arylcyanides, alkylisocyanides, arylisocyanides, amines, phosphines, phosphites, arsines, stibines, nitrogen-containing heterocycles, carbenes, hydride, deuteride, the halides F⁻, Cl⁻, Br⁻ and I⁻, alkylacetylides, arylacetylides, cyanide, cyanate, isocyanate, thiocyanate, isothiocyanate, aliphatic or aromatic alcoholates, aliphatic or aromatic thioalcoholates, amides, carboxylates, aryl groups, $O^{2-}$, $S^{2-}$, carbides, nitrenes, $N^{3-}$, diamines, imines, diimines, diphosphines, 1,3-diketonates 3-ketonates, salicyliminates dialcoholates, dithiolates, borates of nitrogen-containing heterocycles, $\eta^5$-cyclopentadienyl, $\eta^5$-pentamethyl-cyclopentadienyl, $\eta^6$-benzene or $\eta^7$-cycloheptatrienyl, each of which is optionally substituted by one or more radicals R, or ligands which have with the metal a cyclometallated five-membered ring or six-membered ring having at least one metal-carbon bond.

9. A process for the preparation of the compound according to claim 1 which comprises reacting the ligand with metal alkoxides of the formula (64), with metal ketoketonates of the formula (65), with metal halides of the formula (66) or with dimeric metal complexes of the formula (67), M(OR)$_n$  formula (64)

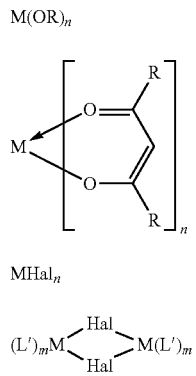

formula (65)

MHal$_n$  formula (66)

$(L')_m M \underset{Hal}{\overset{Hal}{<>}} M(L')_m$  formula (67)

where the symbols M, m, n and R have the meanings indicated in claim 1 and Hal=F, Cl, Br or I.

10. A formulation comprising at least one compound according to claim 1 and at least one solvent.

11. The formulation as claimed in claim 10, wherein the formulation is a solution, a dispersion or a mini-emulsion.

12. An electronic device comprises the compound according to claim 1.

13. An electronic device comprising at least one compound according to claim 1 in at least one layer and wherein the device is selected from the group consisting of an organic electroluminescent device, an organic light-emitting transistor, an organic light-emitting electrochemical cell, an organic light-emitting electrochemical transistor, an organic integrated circuit, an organic field-effect transistor, an organic thin-film transistor, an organic solar cell, an organic optical detector, an organic photoreceptor, an organic field-quench device, an organic plasmon emitting device or an organic laser diode.

14. An electronic device comprising the compound according to claim 1 as emitting compound in one or more emitting layers and the electronic device is an organic electroluminescent device or organic light-emitting electrochemical cell.

15. The compound according to claim 1, wherein the moiety of the formula (2) is selected from the structures of the formulae (9) and (10),

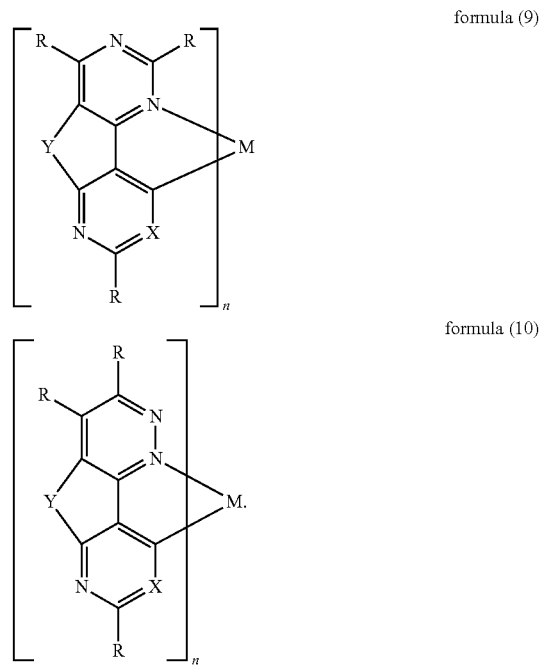

where the symbols and indices used have the meanings given in cm 1.

16. The compound according to claim 1, wherein M is iridium or platinum.

* * * * *